US008603978B2

(12) United States Patent
Strober et al.

(10) Patent No.: US 8,603,978 B2
(45) Date of Patent: Dec. 10, 2013

(54) USE OF MURAMYL DIPEPTIDE (MDP) FOR TREATING INFLAMMATION

(75) Inventors: Warren Strober, Bethesda, MD (US); Ivan Fuss, Kensington, MD (US); Atsushi Kitani, Rockville, MD (US); Peter Mannon, Birmingham, AL (US); Tomohiro Watanabe, Kyoto (JP)

(73) Assignee: The United States of America, as represented by the Secretary, Department of Health and Humand Services, Washington, DC (US)

( * ) Notice: Subject to any disclaimer, the term of this patent is extended or adjusted under 35 U.S.C. 154(b) by 561 days.

(21) Appl. No.: 12/516,633

(22) PCT Filed: Nov. 30, 2007

(86) PCT No.: PCT/US2007/086117
§ 371 (c)(1),
(2), (4) Date: Mar. 3, 2010

(87) PCT Pub. No.: WO2008/070564
PCT Pub. Date: Jun. 12, 2008

(65) Prior Publication Data
US 2010/0292153 A1    Nov. 18, 2010

Related U.S. Application Data

(60) Provisional application No. 60/872,384, filed on Dec. 1, 2006.

(51) Int. Cl.
A61K 38/00    (2006.01)
A61P 1/04     (2006.01)

(52) U.S. Cl.
USPC .......................................................... 514/13.2

(58) Field of Classification Search
None
See application file for complete search history.

(56) References Cited

PUBLICATIONS van Heel DA, et al, "Muramyl dipeptide and toll-like receptor sensitivity in NOD2-associated Crohn's disease," Lancet. May 21-27, 2005;365(9473):1794-6. Genes and Immunity (2005) 6, 637-645.*
Vermeire S. et al, "Current status of genetics research in inflammatory bowel disease," Genes and Immunity (2005) 6, 637-645.*

* cited by examiner

*Primary Examiner* — Thomas Heard
(74) *Attorney, Agent, or Firm* — Swanson & Bratschun, L.L.C.

(57) ABSTRACT

The present invention provides a method of treating or preventing inflammation in a subject comprising administering to the subject an effective amount of a muramyl dipeptide (MDP).

8 Claims, 33 Drawing Sheets

FIG. 2A(ii)

FIG. 2A(iii)

FIG. 2A(iv)

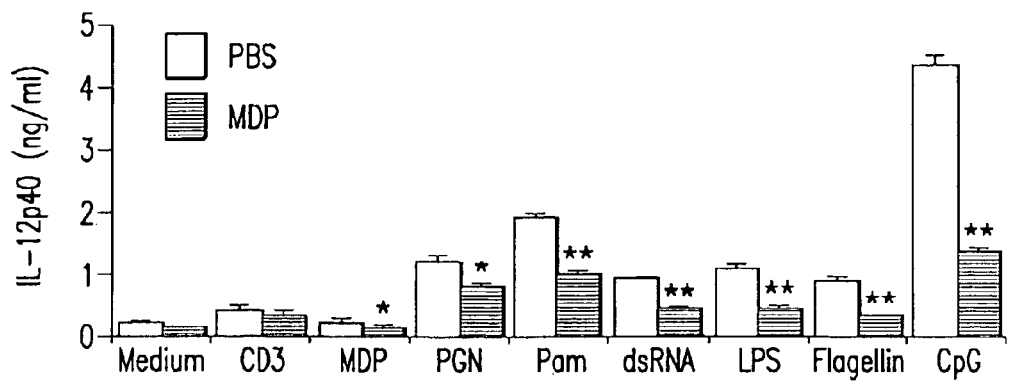
FIG.2B(i)
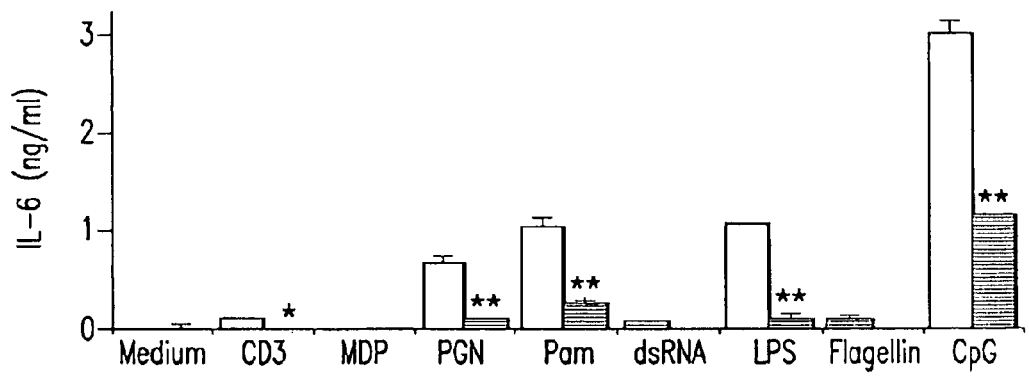
FIG.2B(ii)
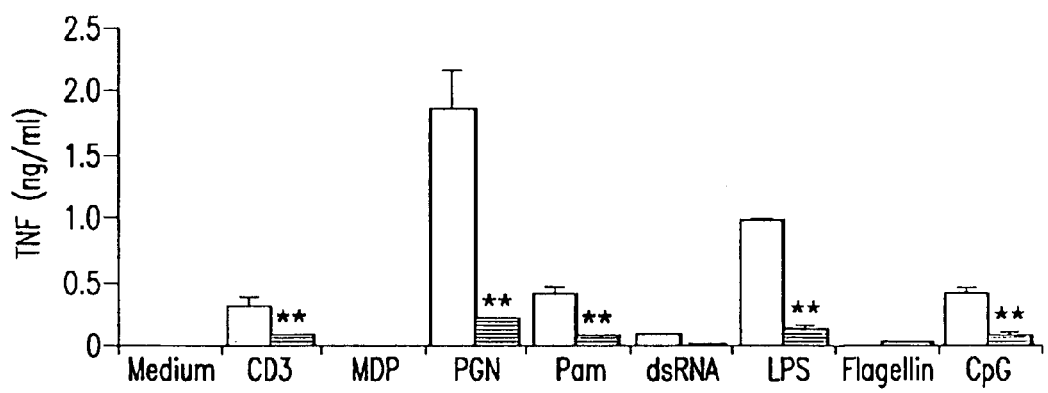
FIG.2B(iii)

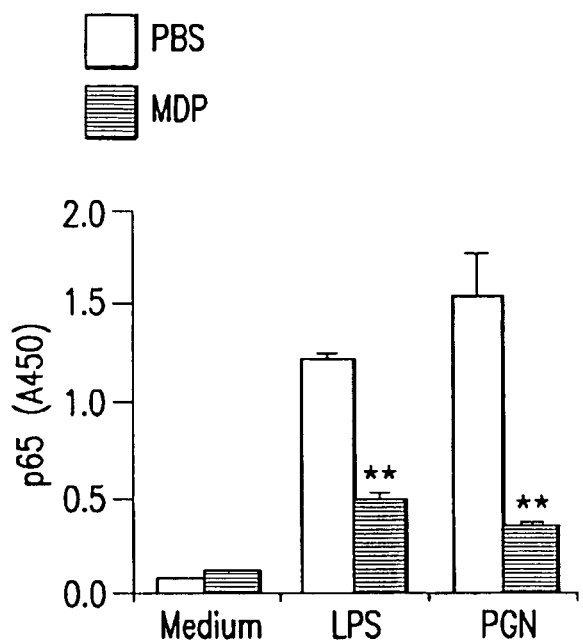
FIG.2E(i)
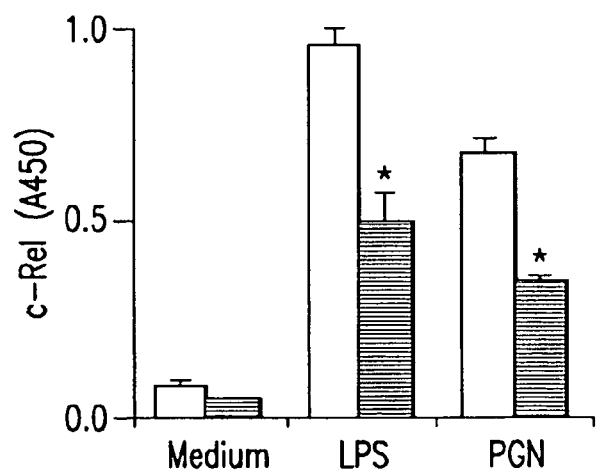
FIG.2E(ii)

FIG. 3B(ii)

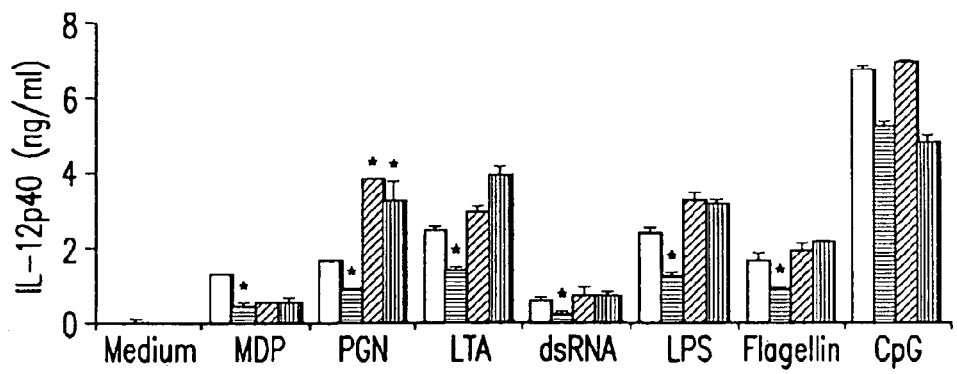
FIG.4A (i)
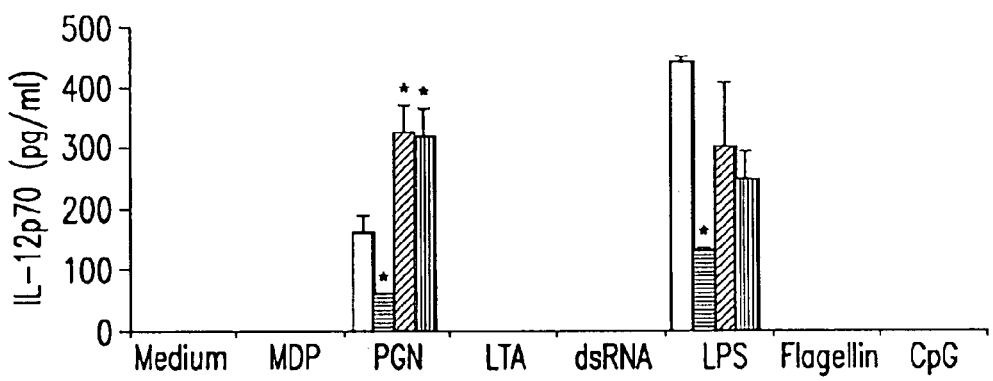
FIG.4A (ii)
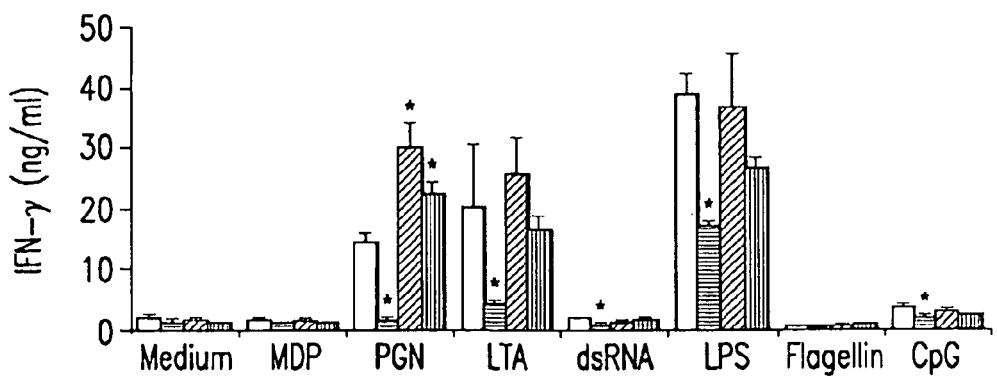
FIG.4A (iii)

FIG.4A (iV)

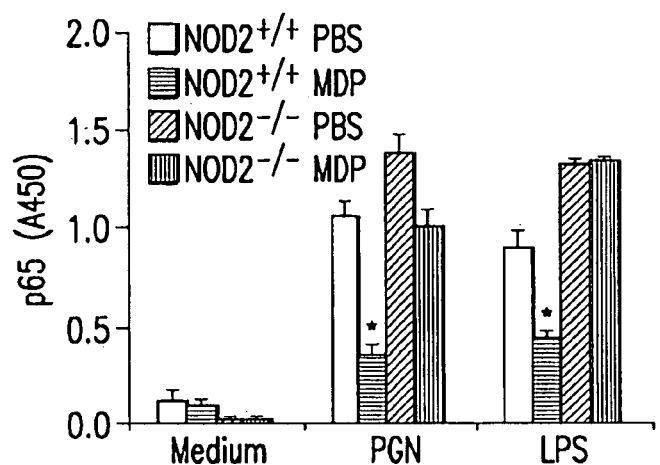
FIG.4C (i)
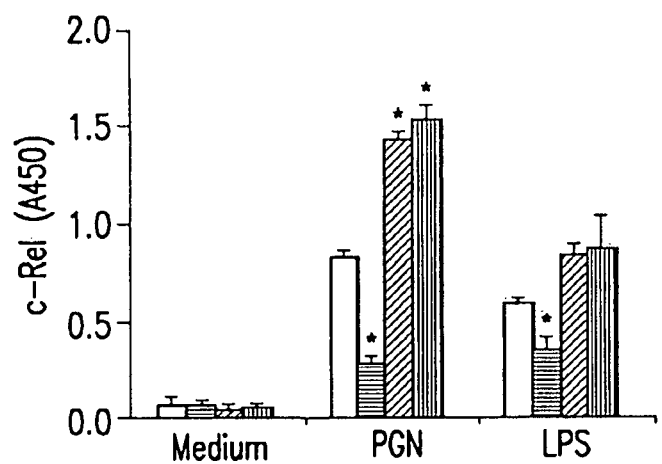
FIG.4C (ii)

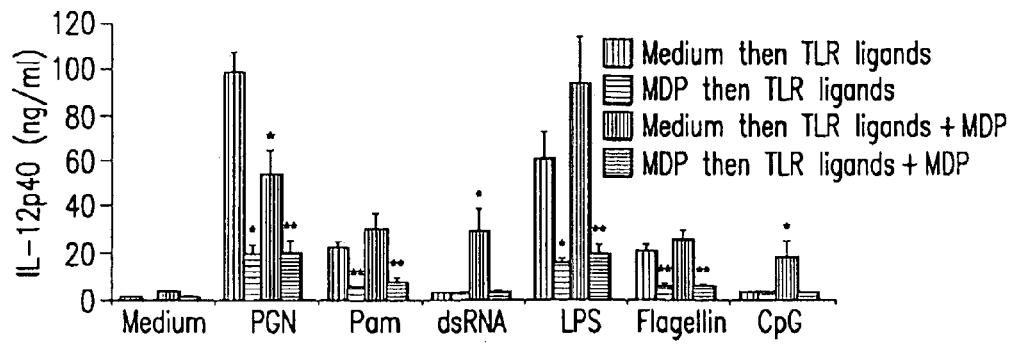
FIG.6A (i)
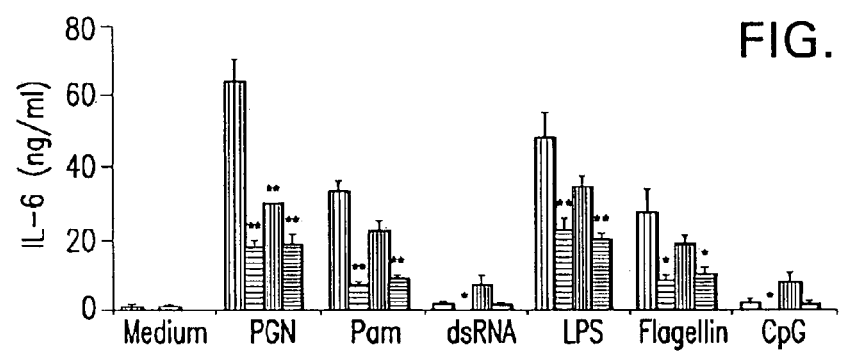
FIG.6A (ii)
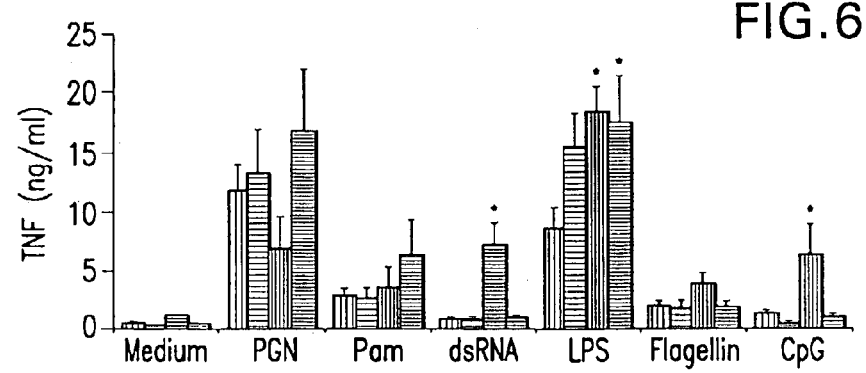
FIG.6A (iii)
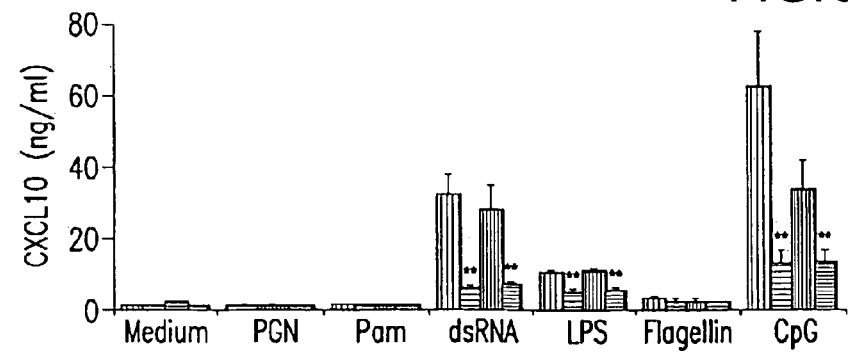
FIG.6A (iV)

FIG.6B (ii)

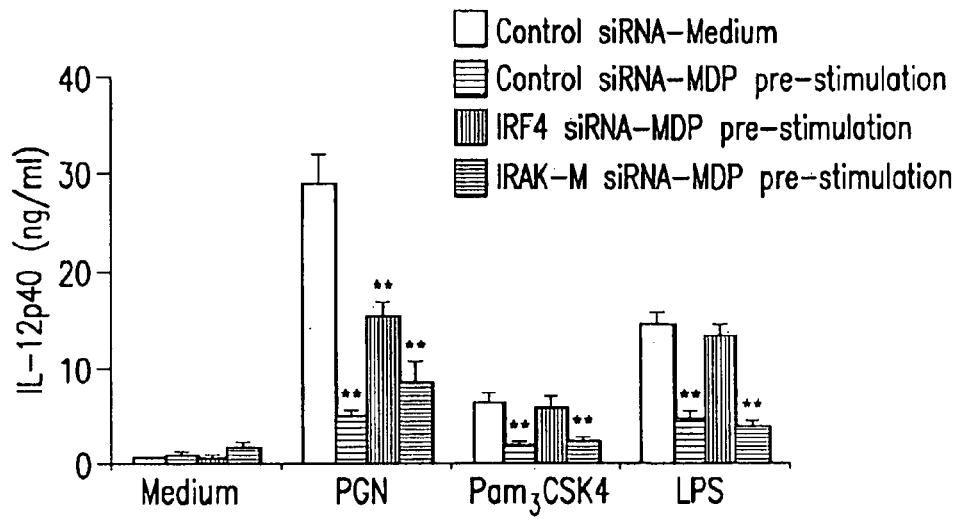
FIG.7D (i)
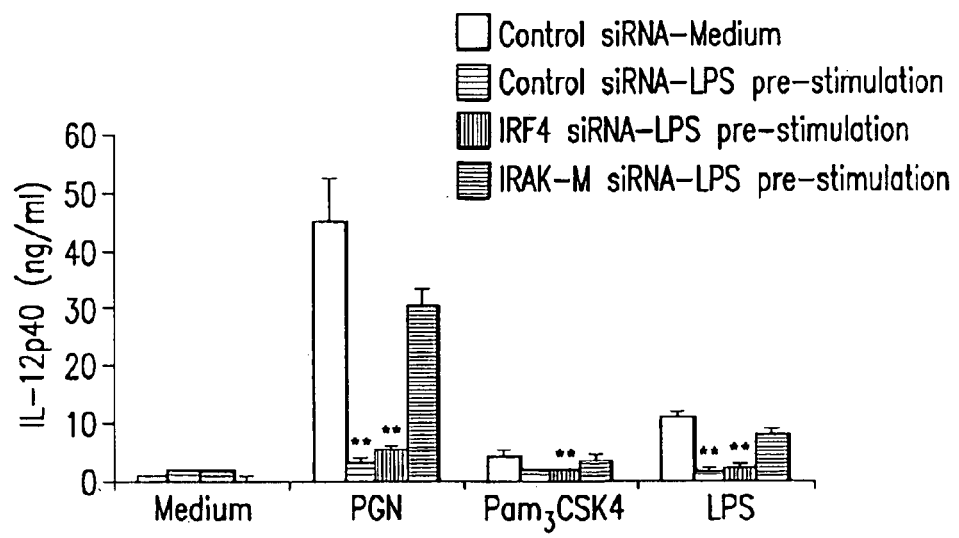
FIG.7D (ii)

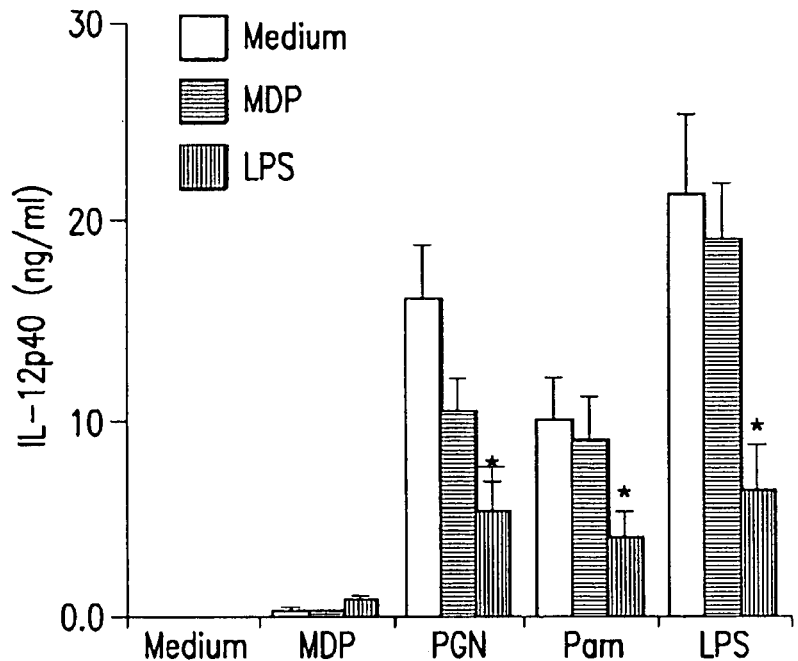
FIG.8B (i)
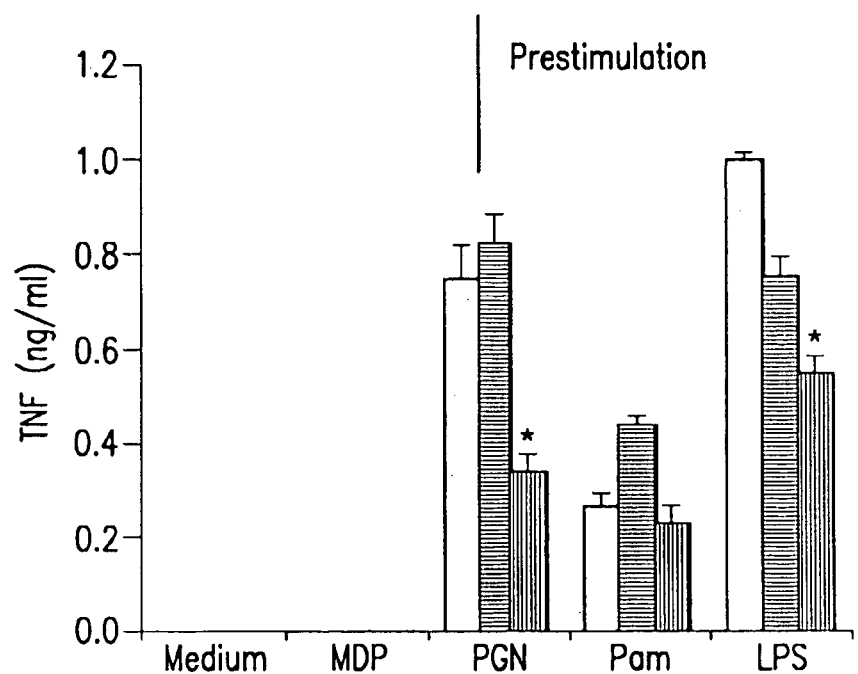
FIG.8B (ii)

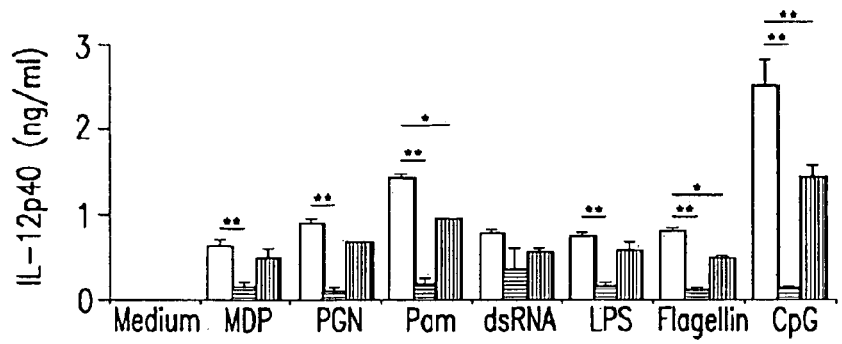
FIG.9D (i)
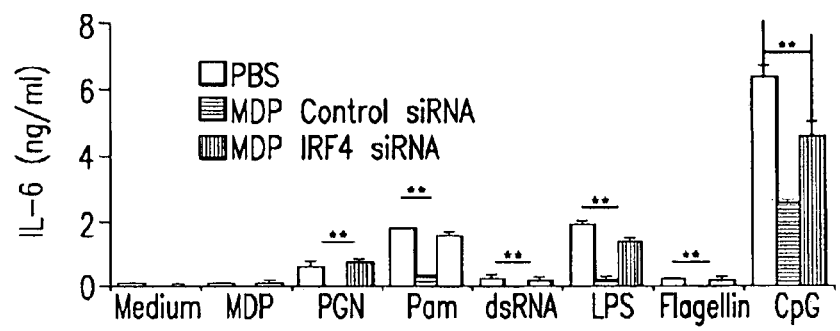
FIG.9D (ii)
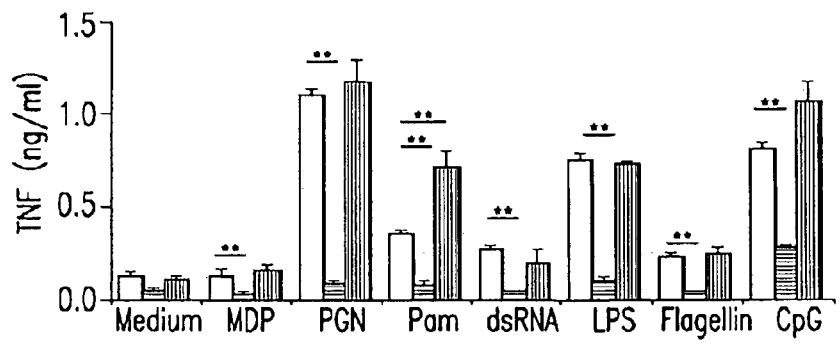
FIG.9D (iii)
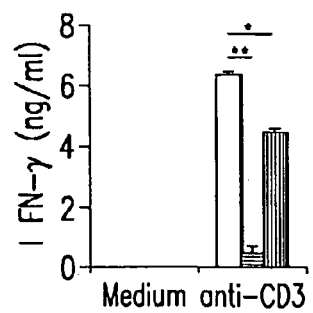
FIG.9D (iV)

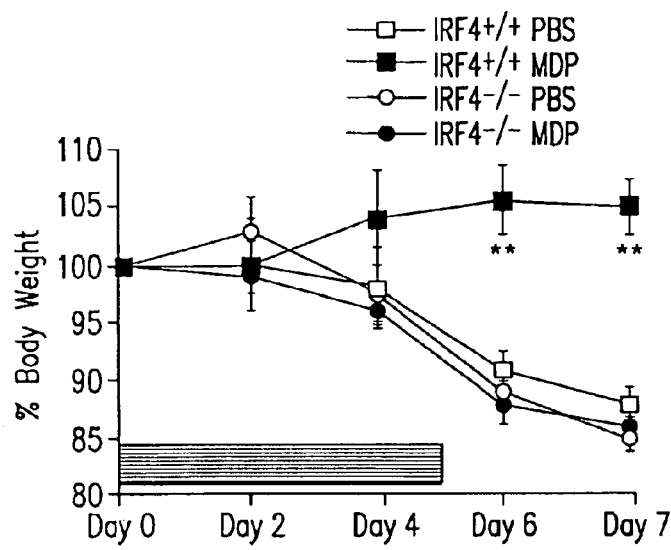
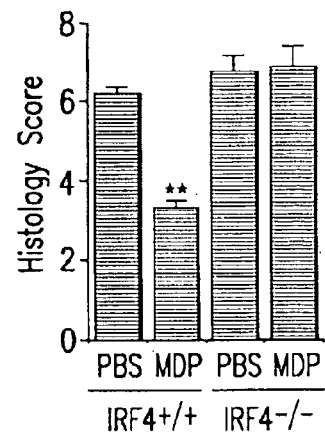
FIG.10A  FIG.10B
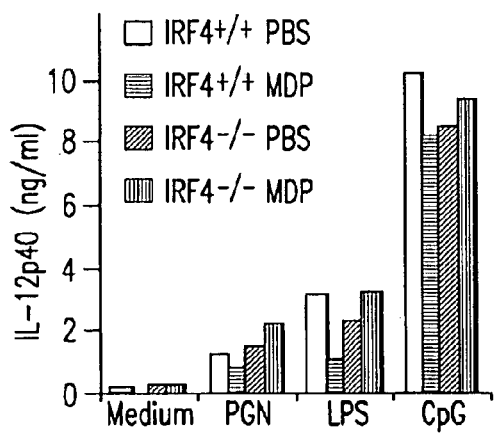
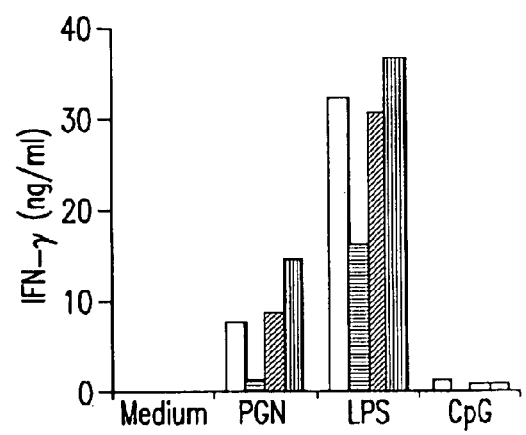
FIG.10C (i)  FIG.10C (ii)

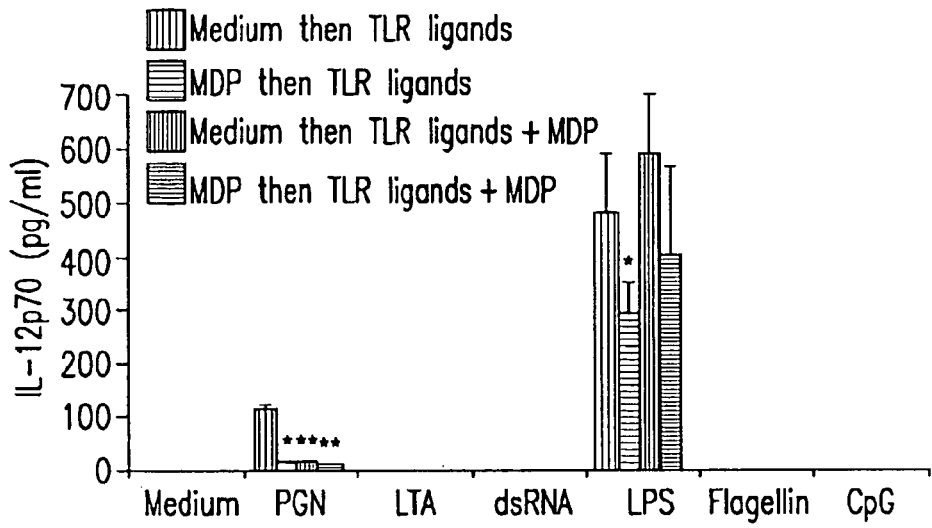
FIG.11A (i)
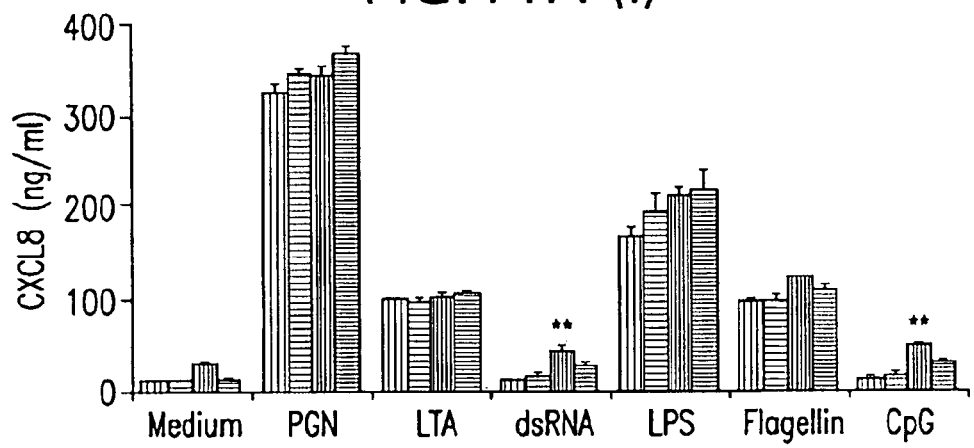
FIG.11A (ii)
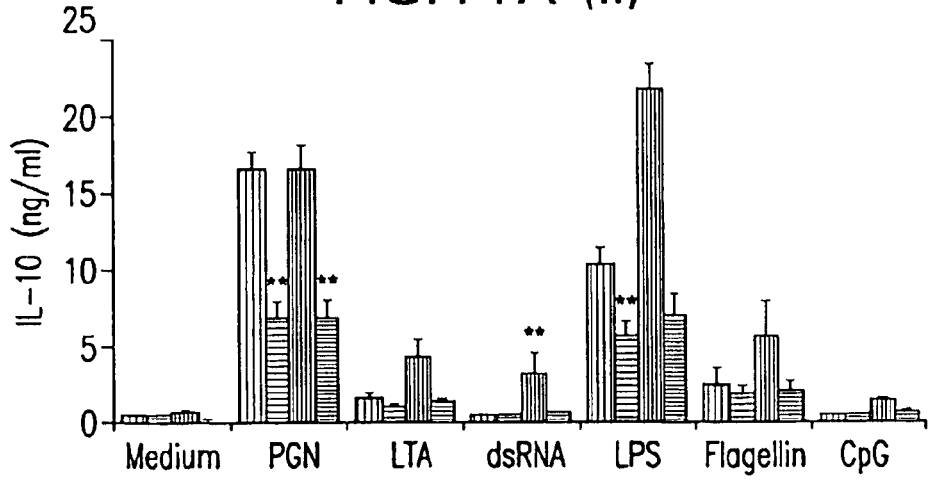
FIG.11A (iii)

FIG.11C (iii)

FIG.11C (iV)

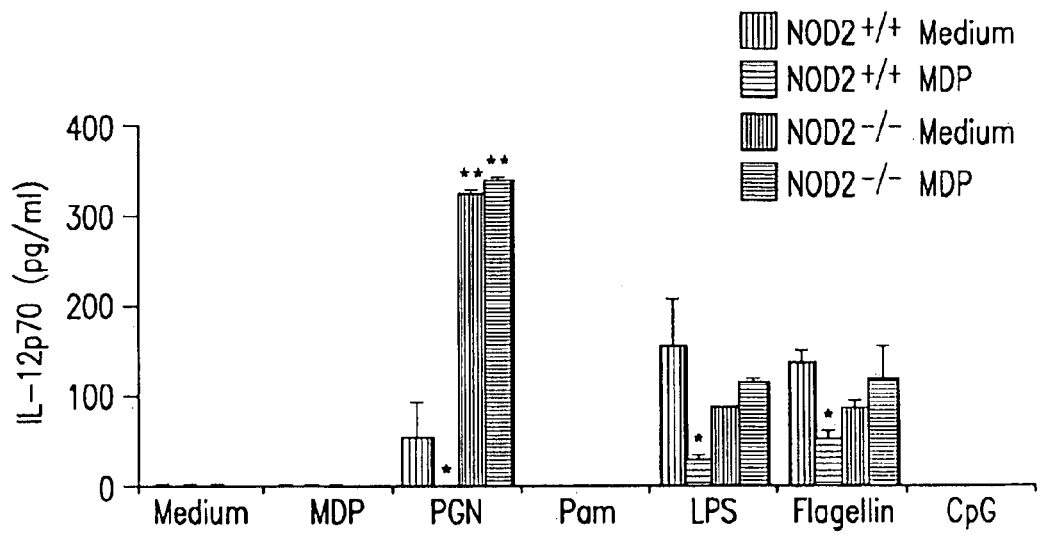
FIG.13A (i)
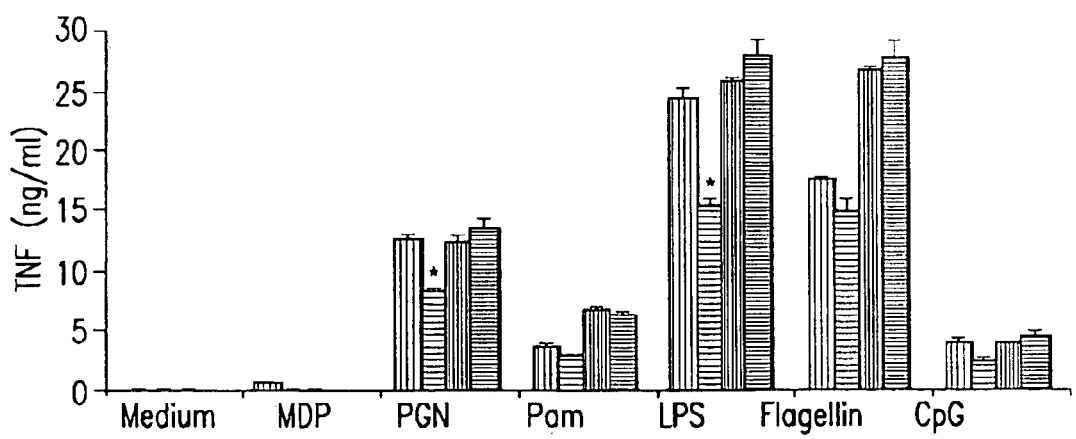
FIG.13A (ii)

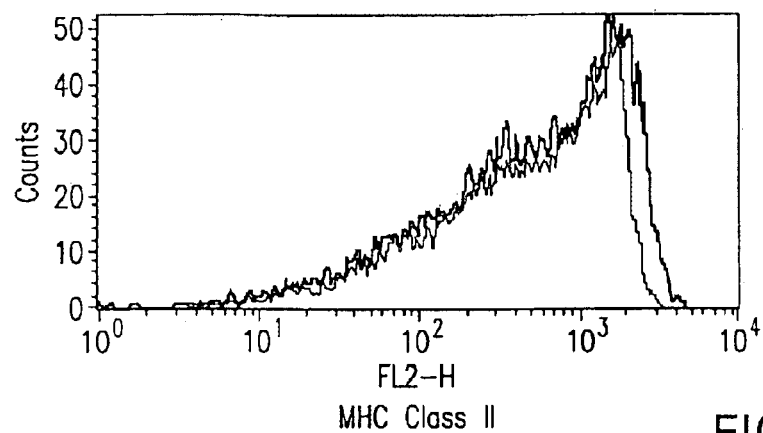
FIG. 13B (i)
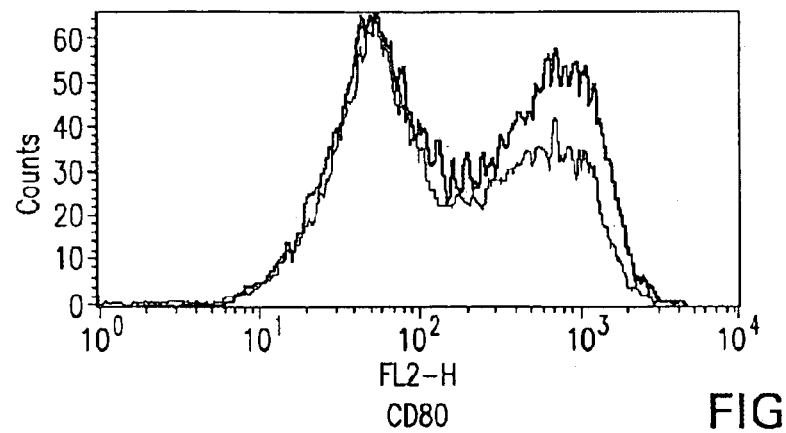
FIG. 13B (ii)
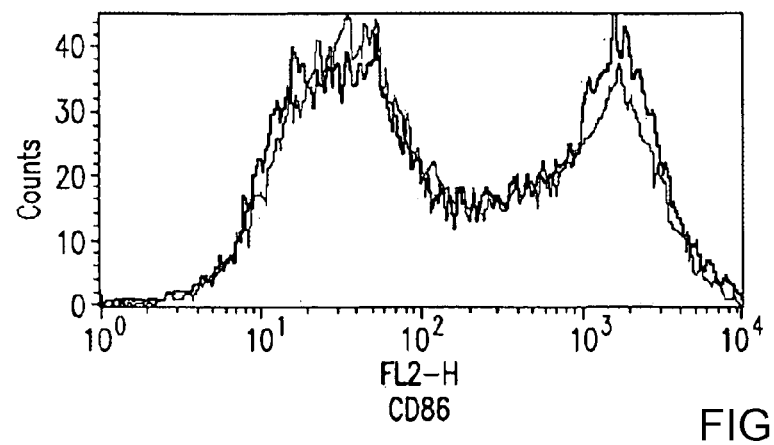
FIG. 13B (iii)

USE OF MURAMYL DIPEPTIDE (MDP) FOR TREATING INFLAMMATION

CROSS-REFERENCE TO RELATED APPLICATIONS

This application is a 35 USC §371 of PCT Application Serial No. PCT/US2007/086117, filed Nov. 30, 2007, entitled "Use of Muramyl Dipeptide Compositions for Treating and Preventing Inflammation," which claims benefit of U.S. Provisional Application No. 60/872,384, filed Dec. 1, 2006, which are each herein incorporated by reference in their entirety.

Incorporated by reference herein in its entirety is the Sequence Listing entitled "14014_0436P1_2007_11_30_Sequence_Listing.TXT", created Dec. 21, 2009, size 2 kilobytes

BACKGROUND OF THE INVENTION

Mediated largely by a family of Toll-like-receptors (TLR) and associated intracellular downstream signaling molecules, the human innate immune response serves multiple functions ranging from providing the first line of defense to coordinating cellular growth as well as other cellular functions. Biochemical studies and genetic analyses using transgenic mice have revealed specific ligands for several TLR receptors. TLR have intracellular domains that can specifically recruit several adaptor proteins including MyD88, TIRAP/MAL, TRIF, and TOLLIP. These adaptor proteins subsequently associate with a family of interleukin-1 receptor-associated kinases (IRAK1, 2, M, and 4). Recruitments of numerous downstream signaling proteins leads to activation of a range of transcription factors such as NF kappa B, AP-1, and IRFs, which are responsible for specific gene transcriptions. Human innate immunity is manifested in diverse cells and tissues. Well-coordinated innate immunity signaling enables human cells and tissues to properly respond to various substances. Improper regulations of such events can lead to excessive signaling via TLRs, thus leading to inflammation. Such inflammation can involve more than one TLR. Therefore, there is a need in the art for new therapies that can modulate one or more TLR in order to reduce inflammation that occurs via multiple TLR pathways.

BRIEF SUMMARY OF THE INVENTION

The present invention provides a method of treating or preventing inflammation in a subject comprising administering to the subject an effective amount of a composition comprising a muramyl dipeptide (MDP). Also provided by the present invention is a method of reducing the symptoms characteristic of inflammation by modulating IRF4 levels and/or activity, comprising administering to the subject an amount of a composition comprising a muramyl dipeptide (MDP) effective in modulating IRF4 levels and/or activity, thereby reducing the symptoms characteristic of inflammation.

Additional advantages of the disclosed method and compositions will be set forth in part in the description which follows, and in part will be understood from the description, or may be learned by practice of the disclosed method and compositions. The advantages of the disclosed methods and compositions will be realized and attained by means of the elements and combinations particularly pointed out in the appended claims. It is to be understood that both the foregoing general description and the following detailed description are exemplary and explanatory only, and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed methods and compositions.

FIG. 10 shows that IRF4 signaling is necessary for the suppression of DSS-colitis. IRF4-intact (IRF4$^{+/+}$) and IRF4-deficient (IRF4$^{-/-}$) mice were treated with 5% DSS in the drinking water for six days (Day 0-5). At an early phase of colitis induction (days 0, 1, 2), mice were administered MDP or PBS (IP). (A) Weight curves of IRF4$^{-/-}$ or IRF$^{+/+}$ mice administered MDP or PBS. ** P<0.01 when compared with PBS-injected IRF4$^{+/+}$ mice. (B) Histology score of IRF4$^{-/-}$ mice treated with PBS or MDP on day 7. (C) MLN cells (1×10$^6$/ml) isolated from IRF4$^{+/+}$ and IRF4$^{-/-}$ mice on day 7 were stimulated with PGN, LPS or CpG; culture supernatants were collected at 48 hrs and analyzed for cytokine production by ELISA.

FIG. 13 shows that MDP pre-stimulation suppresses TLR-induced cytokine secretion in mouse BMDC, but MDP stimulation has no effect on BMDC maturation markers. (A) CD11c+DCs (1×10$^6$/ml) derived from bone marrow cells from NOD2-intact (NOD2+/+) and NOD2-deficient (NOD2−/−) mice were pre-incubated with MDP (50 μg/ml) or medium alone for 24 hrs and stimulated with broad range of TLR ligands. Culture supernatants were collected at 24 hrs and analyzed for cytokine production by ELISA. * P<0.05, ** P<0.01 when sups are compared to NOD2-intact DCs pre-incubated with medium and stimulated with TLR ligands. (B) CD11c+DCs derived from NOD2-intact mice were pre-incubated with MDP (50 μg/ml) or medium alone for 24 hrs and then their co-stimulatory molecules were stained and analyzed by flow cytometry.

DETAILED DESCRIPTION OF THE INVENTION

Figure 1A:
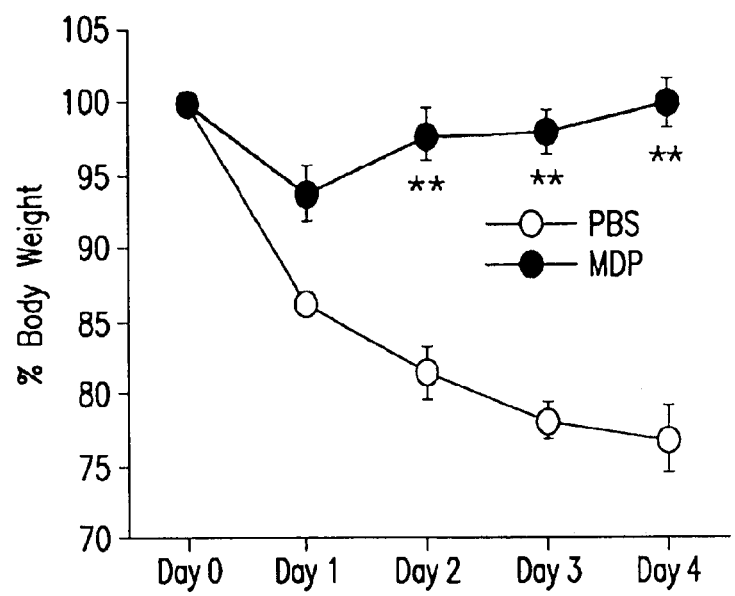
FIG. 1 shows that systemic administration of MDP prevents the development of TNBS-colitis. C57BL/10 mice were administered MDP or PBS (IP; see Examples) on days −3, −2, and −1 and then challenged with intra-rectal TNBS on day 0. (A) Changes of body weight in mice treated with PBS or MDP (n=10) and challenged with intrarectal administration of TNBS. ** $P<0.01$ compared with mice treated with PBS. (B) H&E-stained colonic tissue of the mice harvested on day 4. Histology of PBS-treated mice showed massive infiltration of mononuclear cells as well as destruction of crypt architecture (top); histology of MDP-treated mice showed almost normal colonic tissue with minimal infiltration of mononuclear cells (bottom). (C) Histology score of the colonic tissue of the mice harvested on day 4.

The disclosed methods and compositions may be understood more readily by reference to the following detailed description of particular embodiments and the Examples included therein and to the Figures and their previous and following description. It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise.

Throughout the description and claims of this specification, the word "comprise" and variations of the word, such as "comprising" and "comprises," means "including but not limited to," and is not intended to exclude, for example, other additives, components, integers or steps.

The present invention shows that, surprisingly, muramyl dipeptide compositions can be utilized to effect broad effects on toll-like receptor (TLR) pathways and thus reduce or prevent inflammation. In particular, the present invention shows for the first time that a muramyl dipeptide composition can be administered to a subject to inhibit multiple TLR pathways and thus reduce cytokine responses to multiple TLR ligands through the induction of enhanced IFN-regulatory factor 4 (IRF4) activity. Such broad effects are useful to reduce inflammation in circumstances where inhibition of more than one TLR pathway is desirable to reduce inflammation or reduce other symptoms of a disease associated with inflammation. Such diseases include, but not limited to, an autoimmune disorder, an infection, an allergic disease, transplantation rejection, graft versus host disease, cancer and the like Therefore, the present invention provides a method of treating or preventing inflammation in a subject comprising administering to the subject an effective amount of a composition comprising a muramyl dipeptide (MDP).

By "inflammation" or "inflammatory response" is meant the reaction of living tissues to injury, infection or irritation characterized by redness, warmth, swelling, pain, and loss of function produced, as the result of increased blood flow and an influx of immune cells and secretions. Inflammation is the body's reaction to invading infectious microorganisms and results in an increase in blood flow to the affected area, the release of chemicals that draw white blood cells, an increased flow of plasma, and the arrival of monocytes to clean up the debris. Anything that stimulates the inflammatory response is said to be inflammatory.

As used herein, a "subject" includes animals, for example, a vertebrate. More specifically this vertebrate can be a mammal (e.g., a human, horse, pig, rabbit, dog, sheep, goat, non-human primate, cow, cat, guinea pig or rodent (e.g., a rat or mouse)), a fish, a bird or a reptile or an amphibian. The subject may be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects. The subjects and patients referred to herein can be subjects and patients that have been diagnosed with any of the diseases or disorder set forth herein.

Muramyl Dipeptide Compositions

As set forth above, the methods of the present invention relate to administration of a composition comprising a muramyl dipeptide (MDP). MDP is a muropeptide which is a breakdown product of peptidoglycan (PGN) of Gram-negative and Gram-positive bacteria. It is released during bacterial growth and division, as part of the host response by lysozyme and amidases, or upon antibiotic treatment. After phagocytosis of bacteria or bacterial breakdown products by host immune cells, muropeptides, such as MDP trigger intracellular signaling cascades, leading to altered gene expression and activation of the immune response. Muramyl dipeptide is a natural partial structure of PGN that can be chemically synthesized and modified for use in the methods of the present invention. It can also be derived from PGN.

In the methods of the present invention, a muramyl dipeptide can be muramyl dipeptide, derivative or analog of muramyl dipeptide as well as any other compound that can be modified to produce a muramyl dipeptide.

For example, muramyl dipeptide is commonly known as the muramyl dipeptide structure depicted below (N-acetyl-muramyl-L-alanyl-D-isoglutamine) (Formula I).

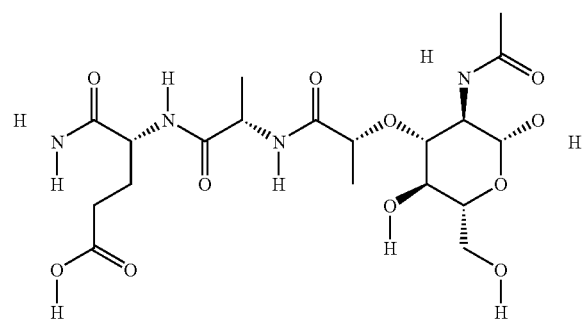

N-acetyl-muramyl-L-alanyl-D-isoglutamine

However, for the purposes of this disclosure, the term "muramyl dipeptide" can also include derivatives of the structure above that have the generic Formula II set forth below:

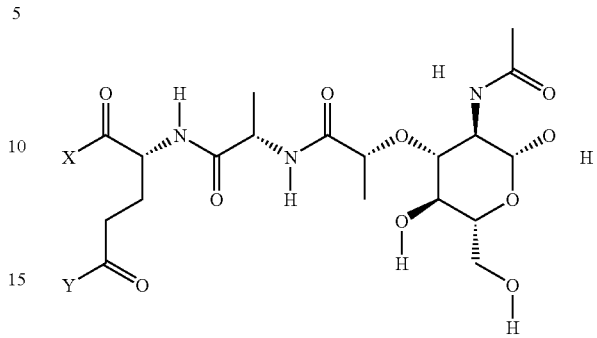

wherein X and Y can each independently be selected from NH2; OH; an alkyl group wherein the alkyl can be straight chain, branched chain or cyclic, having a carbon chain length of from 1 to 20 carbon atoms, unsubstituted or substituted; alkyl esters where the alkyl portion can be straight chain, branched chain or cyclic, having a carbon chain length of from 1 to 20 carbon atoms, unsubstituted or substituted; any one or more of the naturally occurring amino acids; any one or more modified amino acid including for example an amino acid modified with a lipophilic moiety, a dipeptide of any two naturally occurring or modified amino acids, a polypeptide or a lipophilic moiety. Analogs of all of the structures disclosed herein are also provided. Where appropriate, the X and Y can each have any desired stereochemistry. It would be known to one of skill in the art that the stereochemistry depicted in Formulas I and II are not meant to be limiting. It would also be clear to one of skill in the art that modifications to these formulas can result in altered stereochemistry.

Further provided herein as an example of a muramyl dipeptide is a clinically acceptable synthetic derivative of MDP, Murabutide. N-acetyl-muramyl-L-alanyl-D-glutamine can also be used. GlcNac-[N-acetyl-muramyl-L-alanyl-D-isoglutamine], MDP-Lys (N2-[(N-acetylmuramyl)-L-alanyl-D-isoglutaminyl]-N6-stearoyl-L-lysine), is a lipophilic derivative of MDP that can also be used. ImmTher, a liposome-encapsulated lipophilic disaccharide tripeptide derivative of muramyl dipeptide can also be utilized. MDP(Lysyl)GDP, GMTP-N-DPG (N-acetylglucosaminyl-N-acetylmuramyl-L-alanyl-D-isoglutamyl-L-alanyl-dipalmitoylpropylamide), Romurtide, desmuramyl MDP analogue (LK-409), MDP-Lys(L18), muramyl tripeptide cholesterol and B30-MDP are also examples of muramyl dipeptide compositions that can be utilized in the methods of the present invention.

Additional muramyl dipeptide compositions are set forth in U.S. Pat. Nos. 5,877,147, 6,267,968, 5,932,208, 5,534,492, 5,506,204, 5,075,287, 4,663,311, 4,639,512, 4,545,932, 4,427,659, 4,406,890, 4,401,659 and 4,172,125. All of the muramyl dipeptide compounds disclosed in the patents set forth above are hereby incorporated by this reference in their entirety. Other muramyl dipeptide derivatives can be made by acylation, reductive alkylation, sulfonamide formation, urea formation, N-alkylation, or amine addition.

Treatment of Inflammation

By "treat," "treating," or "treatment" is meant a method of reducing inflammation. Such a reduction does not have to be complete and can range from a slight decrease in inflammation to complete amelioration of inflammation or an inflammatory response. This reduction can be a reduction in inflammation associated with a disease or condition such as an autoimmune disorder, an autoinflammatory disease, an infection, an allergic disease, transplantation rejection, graft versus host disease, cancer and the like. In particular, the methods of the present invention can be utilized to reduce inflammation associated with diseases or conditions that involve a reduced or defective IRF4 response which leads to enhanced toll-like receptor (TLR) pathway activity. Therefore, the methods of the present invention can be used to treat inflammation by modulating IRF4 levels and/or activity.

As used herein, an "autoimmune disease" or an "autoimmune disorder" describes a disease state or syndrome whereby a subject's body produces a dysfunctional immune response against the subject's own body components, with adverse effects. This may include production of B cells which produce antibodies with specificity for all antigens, allergens or major histocompatibility (MHC) antigens, or it may include production of T cells bearing receptors that recognize self-components and produce cytokines that cause inflammation. Examples of autoimmune diseases include, but are not limited to, inflammatory bowel disease, multiple sclerosis, rheumatoid arthritis, diabetes mellitus, pernicious anemia, autoimmune gastritis, psoriasis, Bechet's disease, Wegener's granulomatosis, Sarcoidois, autoimmune thyroiditis, autoimmune oophoritis, bullous pemphigoid, phemphigus, polyendocrinopathies, Still's disease, Lambert-Eaton myasthenia syndrome, myasthenia gravis, Goodpasture's syndrome, autoimmune orchitis, autoimmune uveitis, systemic lupus erythematosus, Sjogren's Syndrome, and ankylosing spondylitis.

As used herein "autoinflammatory disease" describes a state of recurrent episodes of systemic inflammation due to dysfunction of the innate immune system. These disorders are caused by primary dysfunction of the innate immune system, without evidence of adaptive immune dysregulation. Innate immune abnormalities include aberrant responses to pathogen associated molecular patterns (PAMPs) like lipopolysaccharide and peptidoglycan, prominent neutrophilia in blood and tissues, and dysregulation of inflammatory cytokines (IL-1beta, TNF-alpha) or their receptors. The autoinflammatory diseases include, but are not limited to, Familial Mediterranean Fever, FMF; Mevalonate Kinase Deficiency, MKD; TNF Receptor Associated Periodic Syndrome, TRAPS; Cryopyrin Associated Periodic Syndrome, CAPS; Blau syndrome; Pyogenic sterile Arthritis, Pyoderma gangrenosum and Acne syndrome, PAPA; and Chronic Recurrent Multifocal Osteomyelitis, CRMO.

As used herein, "allergic disease" describes a disease state or syndrome whereby the body produces a dysfunctional immune response composed of Immunoglobulin E (IgE) antibodies to environmental antigens and which evoke allergic symptoms. Examples of allergic disease include, but are not limited to, asthma, ragweed pollen hayfever, allergy to food substances, atopic eczema, hypersensitivity pneumonitis, Farmers lung, Hyper eosinophilic syndromes and allergic reactions.

As used herein, "graft-versus-host" (GvH) disease describes a disease state or syndrome whereby an immune response is initiated by grafted cells and is directed against the subject's body with adverse effects. Examples of GvH disease include, but are not limited to, acute and chronic GvH disease following bone marrow transplant.

Transplantation rejection describes a disease state or syndrome whereby the transplant recipient's body produces an immune response against the engrafted tissue, resulting in rejection. Transplantation rejection can occur, for example, with kidney, heart, lung or liver transplants as well as with any other transplanted tissue.

An infection is an invasion by and multiplication of pathogenic microorganisms in a bodily part or tissue, which may produce inflammation, subsequent tissue injury and progress to overt disease through a variety of cellular or toxic mechanisms. An infection can be a bacterial infection, a viral infection or a parasitic infection. The infection can be a primary infection or a secondary infection that occurs during or after treatment of another, already existing infection. A secondary infection may result from the treatment itself or from alterations in the immune system.

The term "cancer" or "carcinoma" when used herein refers to or describes a physiological condition, preferably in a mammalian subject, that is typically characterized by unregulated cell growth. Examples of types of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, kidney cancer, gliobastoma, hepatoma, breast cancer, prostate carcinoma, colon carcinoma, head cancer, neck cancer rhabdomyosarcoma, osteosarcoma, leiomysarcoma, myelogenous leukemia, lymphocytic leukemia, multiple myeloma, Hodgkins lymphoma, and B-cell lymphomas. While the term "cancer" as used herein is not limited to any one specific form of the disease, it is believed that the methods of the invention will be particularly effective for cancers which are found to be accompanied by a reduced or deficient IRF4 response which leads to inflammation.

As utilized herein, "modulate or "modulation" means increasing, decreasing or maintaining IRF4 levels. As provided by the present invention and as shown in the Examples, MDP upregulates IRF4. Therefore, MDP can be administered to increase production of IRF4 in cells that produce IRF4, in order to enhance production of IRF4 in the cell. An increase in IRF4 production means that more IRF4 is present in the cell(s) than the amount of IRF4 present in the cell(s), in the absence of MDP. MDP can also be administered to increase production of IRF4 in cells that are deficient in IRF4 production, in cells that cannot maintain levels of IRF4 and in cells that do not produce IRF4. By "modulate" is also meant increasing, decreasing or maintaining IRF4 activity. Therefore, MDP can be administered to increase or maintain levels of IRF4 activity. As utilized herein "IRF4 activity" means, but is not limited to, the ability of IRF4 to reduce inflammation. IRF4 activity is also the ability of IRF4 to reduce inflammation by inhibiting one or more TLR pathways, such as TLR1, TLR2, TLR3, TLR 4, TLR5, TLR6, TLR7, TLR8, TLR 9, TLR10, TLR11, TLR12, TLR13 and any other TLR pathway now known or identified in the future in any species. Therefore, MDP can be administered to increase IRF4 levels and/or activity, thus resulting in inhibition of one or more TLR pathways which leads to inhibition of proinflammatory cytokine (for example, IL-12p40, IL-6 and CXCL10) production. Diseases or conditions that can be treated by modulating IRF4 activity include, but are not limited to, an autoimmune disorder, an autoinflammatory disease, an infection, an allergic disease, transplantation rejection, graft versus host disease, cancer and the like, as described above.

Thus, the present invention provides a method of reducing the symptoms characteristic of inflammation by modulating IRF4 production, comprising administering to the subject an amount of MDP effective in modulating IRF4 production, thereby reducing the symptoms characteristic of inflammation. The present invention also provides a method of reducing the symptoms characteristic of inflammation by modulating IRF4 activity, comprising administering to the subject an amount of MDP effective in modulating IRF4 activity, thereby reducing the symptoms characteristic of inflammation. Inflammation can be accompanied by a number of symptoms, which include, but are not limited to fever, fatigue, weight loss, joint swelling, pain, tenderness, stiffness and skin lesions. One of skill in the art would know which symptoms to observe depending on the type of inflammation being treated.

In the methods of the present invention, treatment can also refer to a method of reducing the disease or condition itself rather than just the symptoms (i.e. inflammation). The treatment can be any reduction from native levels and can be, but is not limited to, the complete ablation of the disease or the symptoms of the disease (e.g., inflammation). Treatment can range from a positive change in a symptom or symptoms of the disease to complete amelioration of the inflammatory response. For example, in the methods of the present invention, treatment can range from a positive change in a symptom or symptoms of, for example, inflammatory bowel disease (IBD) (e.g., inflammation, diarrhea, rectal prolapse, weight loss, abdominal pain etc.) to complete amelioration of the inflammatory response of IBD (e.g., reduction in severity or intensity of disease, alteration of clinical parameters indicative of the subject's condition, relief of discomfort or increased or enhanced function), as detected by art-known techniques. One of skill in the art can readily observe a positive change in a symptom or symptoms of other diseases associated with inflammation.

For example, a method disclosed herein is considered to be a treatment if there is about a 10% reduction in one or more symptoms of the disease in a subject with the disease when compared to native levels in the same subject or control subjects. Thus, the reduction can be about a 10, 20, 30, 40, 50, 60, 70, 80, 90, 100%, or any amount of reduction in between as compared to native or control levels. One of skill in the art can readily observe a positive change in a symptom or symptoms of other disease associated with inflammation.

By "prevent," "preventing," or "prevention" is meant a method of precluding, delaying, averting, obviating, forestalling, stopping, or hindering the onset, incidence, severity, or recurrence of a disease. For example, the disclosed methods are considered to be a prevention if there is about a 10% reduction in onset, incidence, severity, or recurrence of a disease, or symptoms of a disease in a subject with the disease when compared to control subjects. Thus, the reduction in onset, incidence, severity, or recurrence of a disease can be about a 10, 20, 30, 40, 50, 60, 70, 80, 90, 100%, or any amount of reduction in between as compared to control subjects. For example, the disclosed methods are considered to be a prevention for IBD if there is about a 10% reduction in onset, incidence, severity, or recurrence of IBD, or symptoms of IBD (e.g., inflammation, diarrhea, rectal prolapse, weight loss, abdominal pain etc.) in a subject with IBD when compared to control subjects. Thus, the reduction in onset, incidence, severity, or recurrence of IBD can be about a 10, 20, 30, 40, 50, 60, 70, 80, 90, 100%, or any amount of reduction in between as compared to control subjects. One of skill in the art can readily observe a reduction in the onset, incidence, severity, or recurrence of other diseases associated with inflammation.

Throughout this application, ranges will be set forth for dosages, reductions in inflammation and the like. Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Inflammatory Bowel Disease

Although the present invention is not limited to the treatment of inflammatory bowel disease, as stated above, the methods of the present invention can be used to treat or prevent inflammatory bowel disease. Human inflammatory bowel disease (IBD) includes Crohn's disease and ulcerative colitis. Both Crohn's disease and ulcerative colitis are believed to be due to an abnormal mucosal T cell responsiveness to bacterial antigens in the gut lumen. In people with IBD, the immune system reacts inappropriately, mistaking food, bacteria, and other materials in the intestine for foreign or invading substances. In the process, the body sends white blood cells into the lining of the intestines, where they produce chronic inflammation. These cells then generate harmful products that ultimately lead to ulcerations and bowel injury. When this happens, the patient experiences the symptoms of IBD.

It is estimated that as many as one million Americans have IBD—with that number evenly split between Crohn's disease and ulcerative colitis. Currently, there is no medical cure for IBD, however, current medical treatments are aimed at suppressing the abnormal inflammation in the colon lining and thereby controlling the symptoms. The major classes of medication that are currently used to treat IBD include aminosalicylates, corticosteroids, and immunomodulatory medicines. However, aminosalicylates are only effective in treating mild to moderate episodes of ulcerative colitis, steroids are not recommended for long-term use due to side effects, and the current immunomodulatory medications (e.g., Azathioprine, 6-mercaptopurine, and methotrexate) can take as long as three months before their beneficial effects begin to work. New and improved medical treatments are therefore needed to treat and prevent the symptoms of IBD. In particular, broad spectrum treatments, that reduce inflammation by inhibiting several pathways, such as TLR pathways, are especially necessary to maximize inhibition of the inflammatory response. Furthermore, as mentioned above, many treatments for IBD are accompanied by unwanted side effects. Since muramyl dipeptide is a natural byproduct of peptidoglycan that is normally present in a subject, side effects can be minimized by administering a muramyl dipeptide composition or a derivative thereof, that is less likely to be recognized as a foreign substance.

As utilized throughout, "inflammatory bowel disease" (IBD) refers to a chronic recurrent inflammatory disease of unclear etiology affecting the small intestine and colon that includes both Crohn's disease (CD) and ulcerative colitis (UC). Crohn's disease can involve any portion of the intestinal tract but most commonly involves the distal small intestine and/or the colon. Ulcerative colitis involves only the colon, generally limited to the rectum or distal colon. Studies of murine models of CD and UC strongly suggest that both of these diseases are due to dysregulation of the mucosal immune response to antigens in the mucosal microflora (Sartor, R. B. (1995). Gastroenterol Clin North Am 24, 475-507) (Strober W, et al. (2002) Annu. Rev. Immunol. 20:495-549).

One of skill in the art would recognize that ulcerative colitis or indeterminate colitis refers to a condition of the colon characterized by a state of inflammation in which one or more of the following histological characteristics are detectable: a superficial inflammation characterized by the presence of epithelial cell loss and patchy ulceration, pronounced depletion of mucin producing-goblet cells, and reduction of the density of the tubular glands. In addition, in the lamina propia, a mixed inflammatory cell infiltrate consisting of lymphocytes and granulocytes (the latter consisting mostly of neutrophils and, to a lesser extent, eosinophils) associated with an exudation of cells into the bowel lumen is observed. Also, the submucosal level can display marked edema with few inflammatory cells, while in the outer muscle layer one of skill in the art would see little or no evidence of inflammation. See e.g. Boirivant et al. *Journal of Experimental Medicine* 188: 1929-1939 (1998). Clinical symptoms can include, but are not limited to, diarrhea, rectal prolapse, weight loss, abdominal pain, and dehydration.

Crohn's disease refers to inflammation affecting any part of the alimentary tract but most often affecting the terminal part of the small bowel and/or the adjacent ascending colon. Frequently, the inflammation is characterized by "skip lesions" consisting of areas of inflammation alternating with areas of normal mucosa. The affected area of bowel in Crohn's is marked by erythema, edema and increased friability; at times the bowel is strictured and attached to other abdominal organs or to the bowel wall. Fistulae between the affected bowel and other structures including the skin are not infrequent. Microscopic examination of the tissue in Crohn's disease reveals epithelial erosions, loss of mucin-producing goblet cells and an extensive lymphocytic infiltration involving all layers of the mucosa; this infiltrate sometimes contains giant cells indicative of granuloma formation. When inflammation is present for a long time (chronic), it sometimes can cause scarring (fibrosis). Scar tissue is typically not as flexible as healthy tissue. Therefore, when fibrosis occurs in the intestines, the scarring may narrow the width of the passageway (lumen) of the involved segments of the bowel. These constricted areas are called strictures. The strictures may be mild or severe, depending on how much they block the contents of the bowel from passing through the narrowed area. Clinical signs/symptoms of Crohn's disease can include but are not limited to: cachexia, weight loss, poor growth, abdominal pain, draining fistulae, rectal prolapse and dehydration.

Thus, the herein provided methods, comprising administering to a subject a therapeutically effective amount of a composition comprising a muramyl dipeptide can be used to treat or prevent ulcerative colitis. Further, the herein provided methods, comprising administering to a subject a therapeutically effective amount of a composition comprising a muramyl dipeptide, can be used to treat or prevent Crohn's disease, including chronic Crohn's disease.

The present invention shows that patients without NOD2 mutations can be treated with MDP to induce the down-regulation of innate responses to TLR ligands in the gastrointestinal tract. Therefore, also provided herein is a method of treating or preventing inflammatory bowel disease in a subject that does not have a mutation in the CARD15 gene comprising administering to the subject an effective amount of a composition comprising a muramyl dipeptide (MDP).

Thus, it is clear that all of the methods disclosed herein can also comprise a step of diagnosing a subject with an inflammatory disorder and further analyzing the CARD15 gene in the subject to determine whether the subject has a mutation in this gene. If a subject is diagnosed with an inflammatory disorder, for example, inflammatory bowel disease, this subject can also be characterized as not having a mutation in the CARD 15 gene. If a subject is characterized as not having a mutation in the CARD15 gene, this subject can be effectively treated for an inflammatory disorder with a muramyl dipeptide.

Administration

The muramyl dipeptide compositions provided herein can be administered in a number of ways depending on whether local or systemic treatment is desired, and on the area to be treated. The disclosed substances can be administered, for example, orally, intravenously, by inhalation, intranasally, intrarectally, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration, for example, intrarectal administration, can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration include powders or granules, suspensions or solutions in water or non-aqueous media, capsules, sachets, or tablets. Thickeners, flavorings, diluents, emulsifiers, dispersing aids or binders can be desirable.

Some of the compositions can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The substances provided herein can be delivered at effective amounts or concentrations. An effective concentration or amount of a substance is one that results in treatment or prevention of inflammation. Effective dosages and schedules for administering the provided substance can be determined empirically, and making such determinations is within the skill in the art. Those skilled in the art will understand that the dosage of the provided substances that must be administered will vary depending on, for example, the subject that will receive the substance, the route of administration, the particular type of substance used and other drugs being administered. One of skill in the art can utilize in vitro assays to optimize the in vivo dosage of a particular substance, including concentration and time course of administration.

The dosage ranges for the administration of the substances are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

A typical daily dosage of the provided substance might range from about 1 µg/kg to up to 100 mg/kg of body weight or more per day, depending on the factors mentioned above. In one aspect, treatment can consist of a single/daily dosage of 1 mg to 20 mg/kg of body weight of a substance provided herein. In another aspect, the substance is infused during a period from 10 minutes to 48 hours.

The blood pressure, pulse and temperature of the subjects can be monitored prior to and at 30 minute intervals during the two hour infusion period. Subjects can be given a laboratory evaluation consisting of a complete blood count (CBC) with differential, platelet count, SMA-18 chemistry profile, erythrocyte sedimentation rate (ESR) and a C-reactive protein assay at 1) the time of infusion; 2) 24 hours after infusion; 3) 72 hours after infusion; 4) two weeks after the last infusion; 5) four weeks after the last infusion; (6) six weeks after the last infusion; and 7) eight weeks after the last infusion.

When treating a subject with IBD, subjects can also undergo routine colonoscopy with video surveillance at the time of the infusion of a substance provided herein and again at two, four, six and eight weeks after the last infusion. Additionally, serum samples from the subjects can be assayed by ELISA for an inflammatory cytokine(s) (e.g., IL-12, IL-13, IL-23, etc.) levels to monitor drug efficacy. Also, tissue biopsy samples obtained during colonoscopy can be cultured for purified, isolated lamina propia cells and assayed as well. Purified PBM can also be isolated, cultured and assayed.

For example, to evaluate the efficacy of treatment of humans with IBD, such as for example ulcerative colitis or Crohn's disease, with a muramyl dipeptide composition, the following studies can be performed. Patients with active inflammation of the colon and/or the terminal ileum who have failed standard medical therapy, which can include prednisone and/or other immunomodulators known in the art (parenterally or orally) for control of IBD can be selected. Drug efficacy can be monitored via colonoscopy. Patients can be randomized to two different protocols. In one protocol, subjects can remain on initial medication and in the second protocol, subjects can have their medication tapered after receiving the muramyl dipeptide composition.

Following administration of a substance for treating, inhibiting, or preventing IBD, the efficacy of the therapeutic substance can be assessed in various ways well known to the skilled practitioner. For instance, one of ordinary skill in the art will understand that a substance provided herein is efficacious in treating or inhibiting inflammation of an established IBD in a subject by observing that the substance reduces inflammation or prevents a further increase in inflammation. Inflammation can be measured by methods that are known in the art, for example, using tissue biopsies to assess tissue damage or antibody assays (e.g., ELISA) to detect the presence of inflammatory cytokines in a sample (e.g., bodily fluids, but not limited to, blood) from a subject or patient, or by measuring the cytokine levels in the patient.

The substances provided herein can be administered prophylactically to patients or subjects who are at risk for having a disease associated with inflammation. For example, a composition comprising muramyl dipeptide can be administered to a subject at risk of having IBD or who have been newly diagnosed with IBD. In subjects who have been newly diagnosed with IBD but who have not yet displayed an established colitis or the inflammatory response of an established colitis (as measured by biopsy or other assays for detecting the inflammation due to colitis) in blood or other body fluid, efficacious treatment with an substance provided herein partially or completely inhibits the appearance of IBD symptoms and/or onset of UC or CD.

Co-administration

Also disclosed are methods for the treatment or prevention of inflammation comprising co-administering any of the herein provided compositions comprising a muramyl dipeptide with another therapeutic agent. Other therapeutic agents can include, but are not limited to, antibodies, soluble receptors, modified ligands, cytokines, immunomodulatory agents, a chemotherapeutic agent, a chemical, a small or large molecule (organic or inorganic), a drug, a protein, a peptide, a cDNA, a morpholino, a triple helix molecule, a siRNA, a shRNA, an miRNA, an antisense RNA or a ribozyme.

Examples of cytokines, antibodies and immunomodulatory agents that can be employed in the methods provided herein to treat IBD or other diseases associated with inflammation include, but are not limited to, Azathioprine, 6-mercaptopurine, methotrexate, IVIG, IFNα, IFNβ, TNFα Inhibitors (e.g., Enbrel® (entanercept), Remicade® (infliximab) and Humira® (adalimumab)), antisera against lymphocyte membrane antigens (i.e. anti-thymocyte serum (ATS), anti-thymocyte globulin (ATG), anti-lymphocyte serum (ALS), anti-lymphocyte globulin (ALG), anti-CD3, anti-CD4, anti-CD8, anti-IL-4, anti-$\alpha_E\beta_7$, anti-$\alpha_4\beta_7$, anti-$\alpha_4$, anti-IL-12, or anti-IL-13), anti-TNFα, anti-IFN-γ, antisense STAT4 oligonucleotides, anti-ICAM1, antisense ICAM-1 oligonucleotides, anti-CD40L, anti-CD25 (anti-Tac), and IL-10. Examples of soluble receptors that can be employed in the methods provided herein include, but are not limited to, IL-13Rα-Fc and IL-13Rα2-Fc. Examples of modified ligands that can be employed in the methods provided herein include, but are not limited to hIL13 linked to pseudomonas exotoxins (hIL13PE) (e.g. hIL13PE35, hIL13PE38, hIL13PE38 KDEL, hIL13PE40, hIL13PE4E, and hIL13PE38QQR) and mutant hIL13 ligands that compete for IL-13 receptor binding (e.g., hIL-13E13K).

Also disclosed are methods for the treatment or prevention of the inflammatory response of IBD comprising combining the use of any of the herein provided muramyl dipeptide compositions with extracorporeal therapies such as leukocytapheresis and extracorporeal photopheresis (ECP). Extracorporeal therapies are effective for IBDs through immunomodulation, such as a decrease in circulating activated T-lymphocytes and activated granulocytes that play a central role in the pathogenesis of IBD. ECP is a leukapheresis-based immunomodulatory therapy that has been approved by the US Food and Drug Administration for the treatment of cutaneous T-cell lymphoma (CTCL) since 1988. ECP proceeds as follows: A 16-gauge peripheral intravenous line or a temporary central venous access is placed in the patient. Patients undergo discontinuous leukapheresis of 240 mL of leukocyte-enriched blood. This sample (constituting 25-50% of peripheral blood mononuclear cells) is mixed with 300 mL plasma, 200 mL sterile saline, 5000 U heparin, and 200 mcg 8-methoxypsoralen (UVADEX®), which makes the T-lymphocytes more sensitive to ultraviolet (UV) light, more specifically the long wavelength form called UV-A. The preparation is passed as a 1-mm film through a sterile cassette surrounded by UV-A bulbs for 180 minutes, resulting in an average UV-A exposure of 2 J/cm$^2$ per lymphocyte. The mixture is returned to the patient; intravenous access is discontinued. The entire procedure is completed within approximately 4 hours.

Combinations of the cytokines, antibodies, soluble receptors, immunomodulatory agents, and extracorporeal therapies disclosed herein can also be administered to a subject with any muramyl dipeptide composition of the present invention.

Other antibodies, soluble receptors, modified ligands, cytokines, and/or immunomodulatory agents can be administered according to the methods of provided herein both to treat an acute episode of disease or to maintain the subject's condition in a non-inflammatory state.

Pharmaceutically Acceptable Carriers

The muramyl dipeptide compositions provided herein, can be used therapeutically in combination with a pharmaceutically acceptable carrier. By "pharmaceutically acceptable" is meant a material that can be administered to a subject, along with the substance, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, anti-inflammatory agents, anesthetics, and the like.

Suitable carriers and their formulations are described in *Remington: The Science and Practice of Pharmacy* ((19th ed.) ed. A. R. Gennaro, Mack Publishing Company, Easton, Pa. 1995). Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the muramyl dipeptide composition, which matrices are in the form of shaped articles, e.g., films, liposomes or microparticles. It will be apparent to those persons skilled in the art that certain carriers can be more preferable depending upon, for instance, the route of administration and concentration of substance being administered.

Disclosed herein are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a muramyl dipeptide is disclosed and discussed and a number of modifications that can be made are discussed, each and every combination and permutation of the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

It is to be understood that the disclosed methods and compositions are not limited to specific synthetic methods, specified analytical techniques, or to particular reagents unless otherwise specified, and, as such, may vary. It is also to be understood that the terminology used herein is for the purpose of describing particular embodiments only and is not intended to be limiting.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

EXAMPLES

Reagents

Recombinant human and murine GM-CSF, IL-4 were from Peprotech. NOD2 ligand MDP was from Sigma. NOD1 ligand, γDGDAP was synthesized by Peptide Institute (Osaka). Unless otherwise described, the doses of TLR ligands and NOD ligands used for stimulation are as follows; PGN (TLR2 ligand, 10 µg/ml, Fluka), LTA (Lipoteichoic acid, TLR2 ligand, 10 µg/ml), Pam3CSK4 (Pam, TLR2 ligand, 1 µg/ml, InvivoGen), dsRNA (TLR3 ligand, 50 µg/ml, InvivoGen), LPS (TLR4 ligand, 1 µg/ml, Sigma), flagellin (TLR5 ligand, 1 µg/ml, InvivoGen), and CpG (TLR9 ligand, 1 µM, InvivoGen), MDP(NOD2 ligand, 10 µg/ml), γDGDAP (NOD1 ligand, 10 µg/ml).

Induction of Colitis

TNBS colitis was induced in C57BL10 mice obtained from Jackson Laboratories as described previously (34). On day −3, −2, and −1, mice received intraperitoneal injection of MDP (100 µg) or PBS for a total of three times before intrarectal administration of 3.75 mg of TNBS in 100 µl of 45% ethanol. MLN cells and colon LP lymphocytes were isolated on day 3 as described previously (35). Cells ($1 \times 10^6$/ml) were stimulated with anti-CD3 (1 µg/ml, BD Pharmingen) and TLR ligands as described above. In the case of LP lymphocytes, cells were stimulated with TLR ligands in the presence of murine IFN-γ (20 ng/ml, Peprotech). Culture supernatants were collected at 24 hrs and analyzed for cytokine production by ELISA. In some experiments, whole cell extracts were prepared from splenic and MLN CD11b$^+$ cells from mice on day 0 for the analysis of IRF4 expression. CD11b$^+$ cells were isolated as described previously (11). For the induction of DSS-colitis experiments, NOD2-intact, NOD2-deficient, or IRF4-deficient mice (29) were given a range of DSS doses which included 4%, 5% or 5.5% DSS (M.W. 36000-50000, ICN Biomedicals) in the drinking water for six days (day 0-5), and then placed on regular water for two days (day 6-7). Mice were administered MDP (100 µg) (IP) or PBS for a total of three times on day 0, 1, and 2. MLN cells ($1 \times 10^6$/ml) were stimulated with TLR ligands as described above. In the experiments in which mice received intact-NOD2, frameshift-NOD2 or control-empty vector plasmid, the plasmids were encapsulated in Hemagglutinating Virus of Japan (HVJ, GenomIdea) using protamine sulfate according to the manufacturer's protocol. 100 µg/mouse of encapsulated plasmid with 100 µg/mouse of MDP were administrated intraperitoneally on day 0, 1, and 2. Animal use adhered to National Institutes of Health Animal Care Guidelines.

Plasmids Encoding Intact-NOD2 and Frameshift-NOD2

A pcDNA4HisMax plasmid encoding mouse NOD2 complementary DNA was used as intact-NOD2. Mutated-NOD2 plasmid was obtained by inserting a mutation into the intact-NOD2 by the primer 5'-CAGAAGCCCTCCTGCAG-GCCCCTTAAGGGAACAGTGCCATTCTGGAG-3' (SEQ ID NO: 1) and its antisense primer using the QuikChange II XL Site-Directed Mutagenesis Kit (Stratagene). This mouse NOD2 cDNA is equivalent to the human 3020insC Crohn's disease frameshift mutation. This mutated-NOD2 will be referred to as frameshift-NOD2.

Human Monocyte-Derived DCs

Monocytes were elutriated from the peripheral blood of healthy donors and were cultured in 6-well plates ($1 \times 10^6$/ml) in 5 ml of complete medium (RPMI 1640 medium supplemented with 2 mM L-glutamine, and 10% fetal calf serum) supplemented with recombinant GM-CSF (20 ng/ml) and recombinant IL-4 (20 ng/ml). After 3 days of culture, half of the medium in each well was exchanged. After 6 days of culture, >90% of the cells expressed characteristic DC-specific markers (CD1a and HLA-DR), as determined by flow cytometry. After washing twice, cells ($1 \times 10^6$/ml) were incubated with MDP, LPS, CpG or medium for 24 hrs in the absence of GM-CSF and IL-4, and then stimulated with a broad range of TLR ligands in the presence or absence of MDP after washing three times. Culture supernatants were collected at 24 hrs and analyzed for cytokine and chemokine production by ELISA. In some experiments, DCs ($2 \times 10^6$/ml) were transfected with 2 µg of control siRNA, IRF4 siRNA, or IRAK-M siRNA (Santa Cruz Biotechnology) by a human dendritic cell nucleofection kit (Amaxa). DCs were transfected with a mixture of or two individual IRF4-specific siRNAs. The sequences of IRF4-siRNA are as follows: IRF4-siRNA#1; 5'-CUCCUUUCCUAUCUUUACAUU-3' (SEQ ID NO: 2), IRF4-siRNA#2; 5'-GGUAGGUAUUAGUGU-UUGAUU-3' (SEQ ID NO: 3). siRNA-transfected DC were treated with MDP or LPS followed by stimulation with TLR ligands as described above.

Murine BMDCs

BM cells were prepared from NOD2-intact and NOD2-deficient mice (36) and cultured in 6-well plates ($1 \times 10^6$/ml) in 5 ml of complete RPMI medium supplemented with recombinant GM-CSF (20 ng/ml) and recombinant IL-4 (20 ng/ml). After 3 days of culture, half of the medium in each well was exchanged. On day 6, cells were harvested and sorted by anti-mouse CD11c magnetic beads (Miltenyi Biotech) as described previously (37). CD11c$^+$ DCs ($1 \times 10^6$/ml) were incubated with MDP (50 µg/ml) or medium for 24 hrs and then stimulated with a broad range of TLR ligands as described above. Culture supernatants were collected at 48 hrs and analyzed for cytokine production by ELISA. In some experiments, CD11c$^+$ DCs ($2 \times 10^6$/ml) pre-incubated with MDP or medium were co-cultured with splenic CD4$^+$ T cells ($1 \times 10^6$/ml) isolated from OT-II transgenic mice (Jackson laboratories) (38) in the presence of OVA$_{323-339}$ peptide (0.5 µM) and TLR ligands as described above. Splenic CD4$^+$ T cells were purified with the use of anti-mouse CD4 magnetic beads (Miltenyi Biotech) as described previously (39). Culture supernatants were collected at 60 hrs and analyzed for cytokine production by ELISA. In the experiments staining for surface co-stimulatory molecules, CD11c+ DCs from NOD2-intact mice were incubated with MDP (50 µg/ml) or medium for 24 hrs and then stained with anti-CD80, anti-CD86 (eBioscience), and anti-MHC classII (Milltenyi) followed by flow cytometric analysis.

Immunoprecipitation

HEK293 cells (ATCC) ($1 \times 10^6$/cells) were transfected with 2 µg of FLAG-tagged human IRF4 vector together with 2 µg of human MyD88, TRAF6, RICK, NOD2 vector (Invivo-Gen), or TRAF2 vector (Origene) by Trans IT LT1 (Minis). Whole cell lysates were prepared 48 hrs after the transfection and were incubated with anti-FLAG conjugated beads (Sigma) overnight. In some experiments, human DCs were incubated with anti-IRF4 Ab (Santa Cruz Biotechnology) and protein A/G plus agarose (Santa Cruz Biotechnology).

Luciferase Assay

HT-29 cells (ATCC, $1 \times 10^6$/ml) were transiently transfected with the reporter plasmid pNF-κB-Luc containing four κB binding sites (Clontech) and pSV-β-Galactosidase vector (Promega), together with a plasmid expressing MyD88, TRAF6, RICK, IRF4 by Trans-IT LT1 reagent. After overnight incubation with serum-free medium, cell lysates were analyzed for luciferase activity (Promega) and galactosidase activity (Applied Biosystems) for normalization. The luciferase activity was normalized for transfection efficiency and mentioned as "NF-κB activation fold" in text.

Human Monocytic Cell Lines

Two human monocytic cell lines, THP1 and Monomac6 cells were used. Cells ($5\times10^5$/ml) were pre-incubated with MDP, LPS or medium for 24 hrs and stimulated with TLR ligands after washing three times. Culture supernatants were collected at 24 hrs and analyzed for cytokine production by ELISA. In some experiments, THP1 and human DCs were transfected with a vector expressing human IRF4 cDNA or a control vector by Amaxa followed by the stimulation with MDP and TLR ligands.

IRF4 siRNA Study in TNBS-colitis

Sequences of siRNAs are as follows: control siRNA, 5'-UAAGGCUAUGAAGAGAUACUU-3' (SEQ ID NO: 4); IRF4 siRNA, 5'-GGACACACCUAUGAUGUUAUU-3' (SEQ ID NO: 5). These siRNAs were obtained from Dharmacon. For in vivo transfection, 1 mg of siRNA was encapsulated in HVJ as previously described (11, 21, 34). C57BL10 mice that were treated with MDP during day −3 and −1 were intrarectally administered 100 μg of IRF4 or control siRNA encapsulated in HVJ-E for a total of four times on day −2, −1, 0, and 1.

Histological Analysis

Colon was harvested at the indicated time point. Colon tissues were stained with hematoxylin and eosin (H&E) and used for the scoring of the inflammation as described by Obermeier et al. for DSS colitis (40) and Neurath et al. for TNBS colitis (41). Histology was scored for DSS colitis as follows: epithelium (E), 0=normal morphology; 1=loss of globlet cells, 2=loss of globlet cells in large areas; 3=loss of crypts; 4=loss of crypts in large areas. For infiltration (I), 0=no infiltrate; 1=infiltrate around crypt basis; 2=infiltrate reaching to L. muscularis mucosae; 3=extensive infiltration reaching the L. muscularis mucosae and thickening of the mucosa with abundant edema; 4=infiltration of the L. submucosa. The total histological score is given as E+I. Histology was scored for TNBS colitis as follows, 0=no sign of inflammation, 1=very low level, 2=low level of leukocytic infiltration, 3=high level of leukocytic infiltration, high vascular density, thickening of the colon wall, 4=trasmural infiltrations, loss of goblet cells, high vascular density, thickening of the colon wall.

ELISA

Protein concentrations of cytokines and chemokines were determined by BD Pharmingen ELISA kits for assay of human IL-12p40, human IL-12p70, human TNF, human IL-10, human CXCL8, human CXCL10, mouse IL-12p40, mouse IL-12p70, mouse IL-6, and mouse IFN-γ, eBioScience kits for assay of human IL-6, and Biosource kits for assay of mouse serum amyloid A.

Western Blot Analysis

Cell lysis and blotting was done as described (11). The membrane was blotted with Abs as follows; anti-TAK1, MyD88, TRAF6, IRF3, SOCS-1, anti-mouse IRF4 (Santa Cruz Biotechnology), anti-human IRF4, anti-IRAK-M, anti-IKKγ (Cell Signaling), anti-IRF5 (abcam), RICK (Cayman chemicals).

Gel-Shift Assays

Nuclear extracts were prepared from human DCs pre-incubated with MDP or medium for 24 hrs and stimulated with TLR ligands for 2 hrs. In colitis experiments, MLN cells isolated from the mice at the indicated time points were stimulated with TLR ligands for 2 hrs and then nuclear extracts were prepared. Nuclear extracts was obtained with the use of Transfactor extraction kit (Clontech). Analysis of NF-κB activation by gel-shift assay was performed according to the protocol contained in the Gel-shift NF-κB kit (Active Motif). Analysis of p65 and c-Rel activation was measured by TransAM Kit (Active Motif).

Statistical Analysis

Student's t test was used to evaluate the significance of the differences. Statistical analysis was performed with the Stat-View v.4.5 program (Abacus Concepts). A value of $P<0.05$ was regarded as statistically significant. Results are presented as means±S.E. unless otherwise described.

Administration of MDP Protects Mice from TNBS-Colitis

Figure 1B:
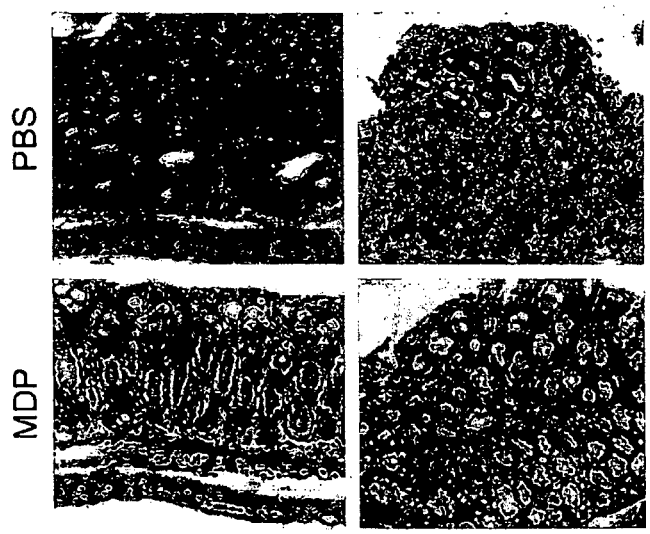
Figure 1C:
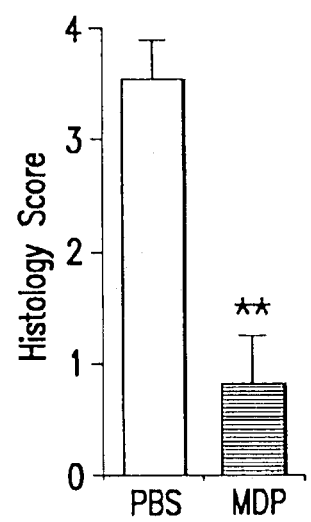

In the present studies, the hapten-induced colitis induced by administration of TNBS, C57BL/10 mice were administered MDP (100 μg IP) or PBS (IP) for three consecutive days (day −3 to −1) prior to intra-rectal injection of 3.75 mg of TNBS in 45% ethanol (day 0). As shown by the body weight curves depicted in FIG. 1A, MDP administration prior to the TNBS challenge protected mice from the loss of weight normally seen during the development of TNBS-colitis. Moreover, as shown in FIG. 1B, whereas mice that were administered PBS prior to intra-rectal TNBS instillation exhibited destruction of crypt architecture and infiltration of mononuclear cells in the colonic lamina propria (LP) in tissue examined on day 4 after challenge with TNBS, mice that were administered MDP prior to intra-rectal TNBS instillation, exhibited little epithelial damage or cellular infiltration. As shown in FIG. 1C, this was confirmed by the colitis scores. Thus, these data show that MDP administration prior to TNBS challenge can inhibit the development of TNBS-colitis.

Figure 2A:
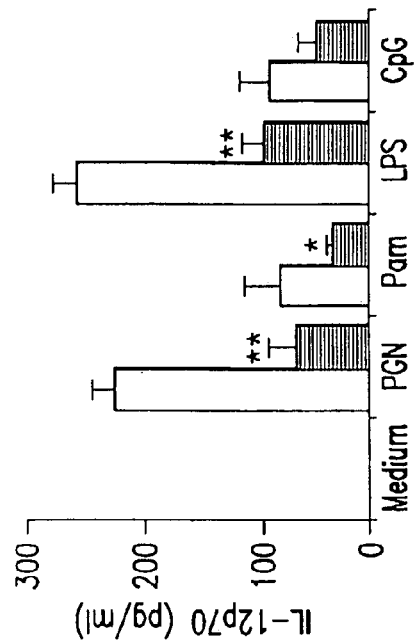
FIG. 2 shows that MDP administration reduces the TLR-induced cytokine responses of MLN and colonic LP cells from mice with TNBS-colitis. (A) Colon LP lymphocytes ($1\times10^6$/ml) isolated from the mice on day 3 were stimulated with PGN, Pam$_3$CSK4, LPS, and CpG in the presence of IFN-γ (20 ng/ml); culture supernatants were collected at 48 hrs and analyzed for cytokine production. * $P<0.05$, ** $P<0.01$ when sups from MDP-treated mice are compared with sups from PBS-treated mice. (B) MLN cells ($1\times10^6$/ml) isolated from mice with TNBS-colitis on day 3 were stimulated with anti-CD3 (1 μg/ml) and broad range of TLR ligands. Culture supernatants were collected at 48 hrs and analyzed for cytokine production. * $P<0.05$,  $P<0.01$, when supernatantss of MDP-treated mice are compared with supernatants of PBS-treated mice. (C) MLN cells and colon LP lymphocytes isolated from the mice on day 3 were stimulated with anti-CD3 (1 μg/ml); culture supernatants were collected at 48 hrs and analyzed for IFN-γ production.  $P<0.01$ when supernatants from MDP-treated mice are compared with supernatants from PBS-treated mice. (D) Evaluation of NF-κB activation in MLN cells isolated from the mice on day 3 and stimulated with LPS or PGN. Nuclear extracts were prepared from MLN cells isolated from PBS or MDP-treated mice and stimulated with LPS or PGN for 2 hrs and then subjected to EMSA. (E) Nuclear extracts obtained in (D) assayed for p65 and c-Rel activation using NF-κB transcription factor ELISA. * $P<0.05$, ** $P<0.01$ compared to the nuclear extracts from PBS-treated mice.
Figure 2A:
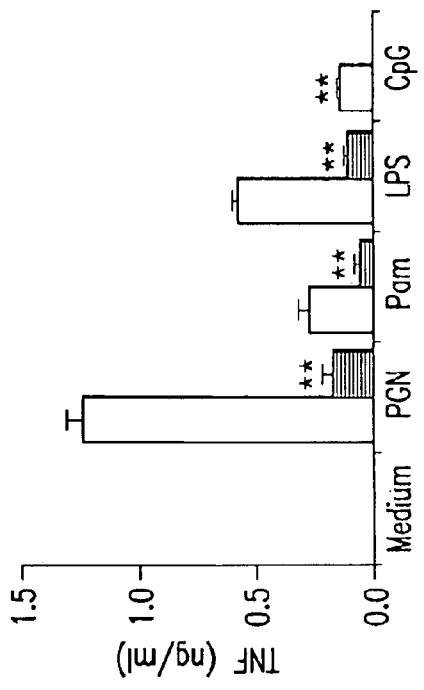
Figure 2A:
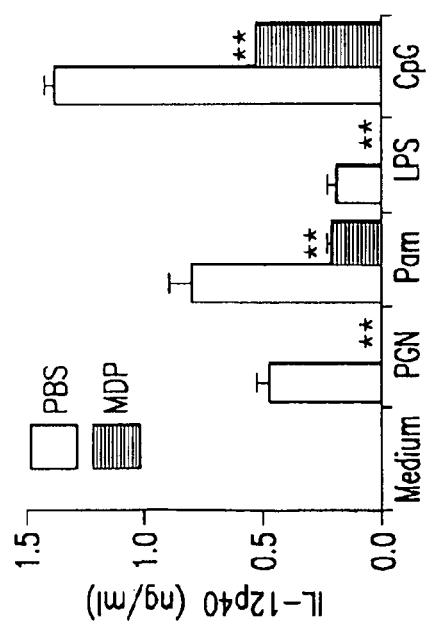
Figure 2A:
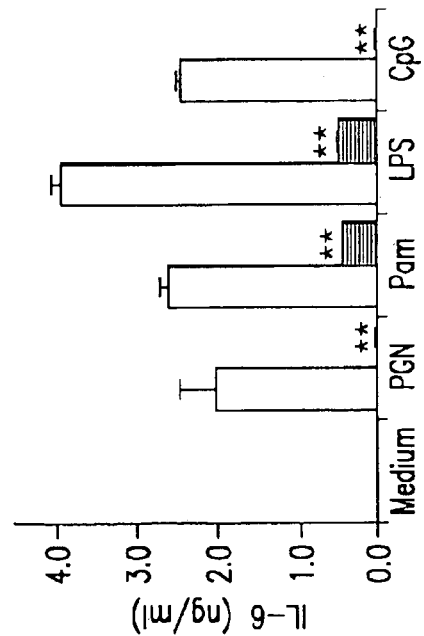
Figure 2C:
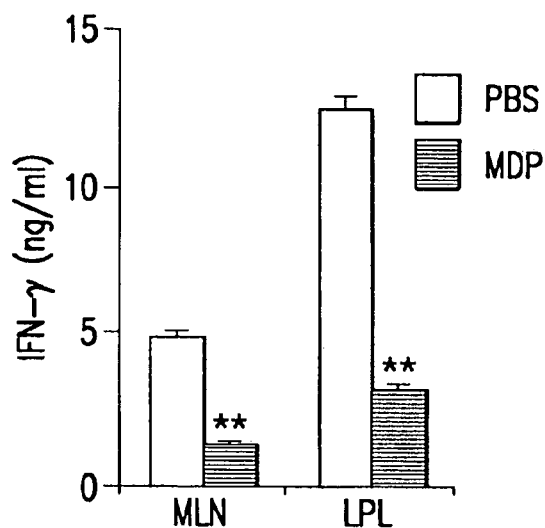
Figure 2D:
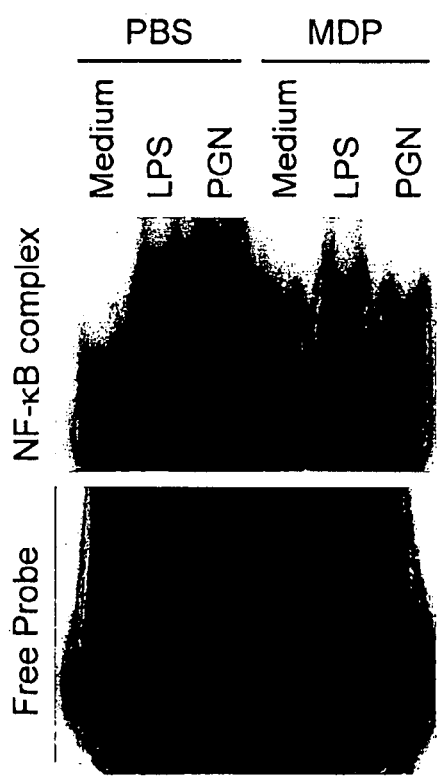

Whether or not the prevention of colitis development is associated with reduced inflammatory cytokine responses to microbial Ags, i.e. TLR and NLR ligands was determined. For this purpose, mesenteric lymph nodes (MLNs) and LP cells isolated from mice pre-treated with MDP or PBS before TNBS challenge were stimulated with a broad range of TLR ligands. As shown in FIGS. 2A and 2B, MLN cells and colonic LP cells obtained from mice administered MDP and then stimulated with a broad range of TLR ligands displayed markedly reduced production of IL-12p40, IL-12p70, IL-6, and TNF upon stimulation with TLR2, TLR3, TLR4, TLR5, and TLR9 ligands as compared with cells obtained from mice administered PBS before TNBS challenge. Thus, prior activation of NOD2 by MDP administration causes suppression of multiple TLR pathways, not just TLR2. Furthermore, these reduced innate cytokine responses are associated with reduced adaptive Th1 responses since, as shown in FIG. 2C, MLN and colonic LP cells from MDP-treated mice exhibited a markedly reduced IFN-γ production upon anti-CD3 stimulation. It was next determined whether reduced cytokine responses were due to the down-regulation of NF-κB activation. Accordingly, nuclear proteins were isolated from MLN cells and assessed such activation by both EMSA and a semi-quantitative method based on the binding of the extract to an NF-κB consensus sequences followed by detection of bound components with subunit-specific antibodies (NF-κB ELISA study) (11). As shown in FIGS. 2D and 2E, NF-κB activation by lipopolysaccharide (LPS) or PGN stimulation is suppressed in MLN cells from MDP-treated mice as compared to those from PBS-treated mice. Taken together, these data show that MDP treatment can protect TNBS-colitis by inhibiting responses to a wide range of TLR ligands.

Administration of MDP Protects Mice from Dextran Sodium Sulfate (DSS)-Colitis

Figures 3A, 3B:
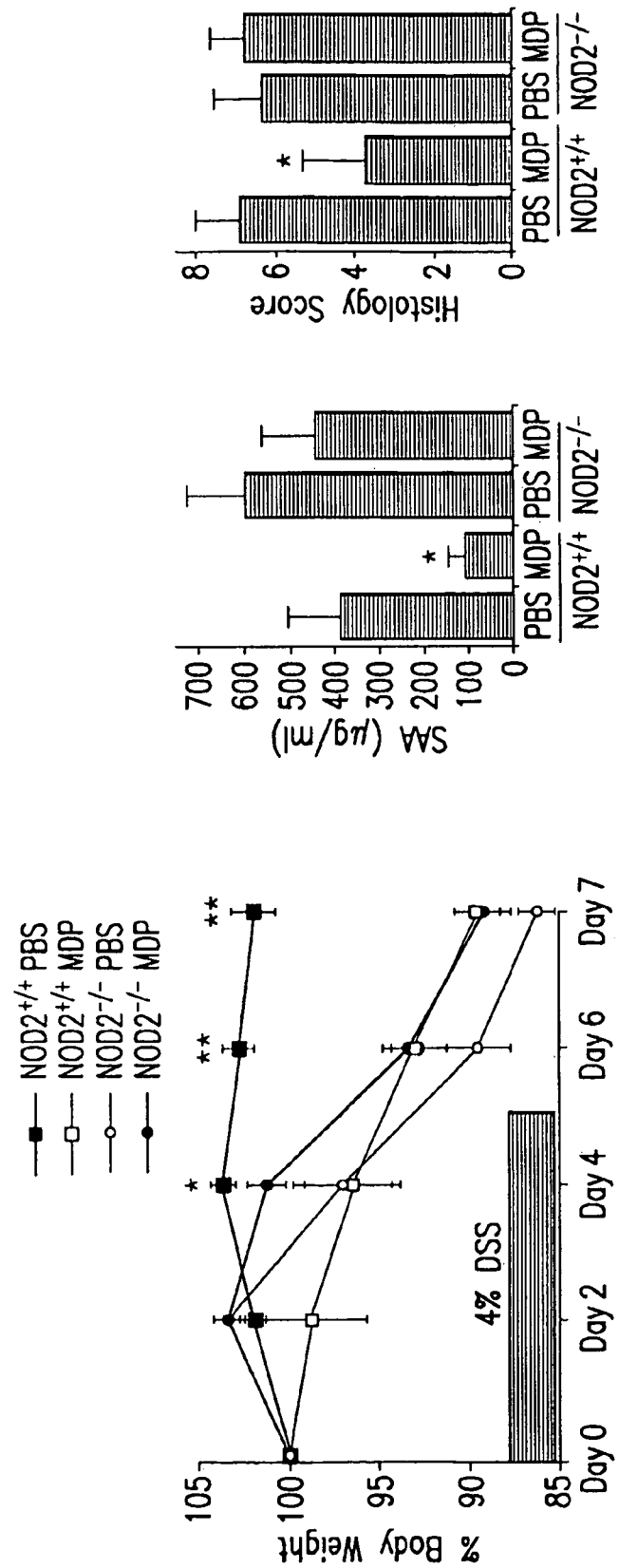
FIG. 3 shows that MDP administration prevents DSS-colitis. NOD2-intact (NOD2$^{+/+}$) and NOD2-deficient (NOD2$^{-/-}$) mice were treated with drinking water containing 4% DSS for six days (Day 0-5). At the early phase of colitis induction (day 0, 1, 2), mice were administered MDP (IP) or PBS every day. (A) Changes of body weight in PBS or MDP-injected mice. * $P<0.05$, ** $P<0.01$ when time point values of NOD2-intact mice administered MDP compared with NOD2-intact mice administered PBS. (B) Serum amyloid A (SAA) levels and colitis scores of mice (see Examples) on day 7. SAA levels were determined by ELISA. * $P<0.05$ when NOD2-intact mice administered MDP compared with mice administered PBS.

In studies of a second experimental colitis, DSS-colitis, control NOD2-intact or NOD2-deficient mice treated with 4% DSS in the drinking water from day 0 to day 5 to induce the colitis were administered either MDP (100 μg IP) or PBS (IP) for three consecutive days at the early phase of the colitis (day 0, 1, 2). As shown in FIG. 3A, NOD2-intact mice with DSS-colitis treated with PBS but not those treated with MDP exhibited significant body weight loss during the observation period. Furthermore, this protective effect was mediated by NOD2 activation since NOD2-deficient mice with DSS-colitis exhibited comparable body weight loss if they were treated with PBS or MDP. As shown in FIG. 3B, these body weight data correlated with serum amyloid A levels as well as with the colitis scores of the NOD2-intact mice treated with MDP and PBS and, again, no difference was seen in these parameters in NOD2-deficient mice treated with MDP or PBS. Thus, these studies provide strong evidence that MDP administration can protect mice from the development of DSS-colitis, and complement the data above on TNBS-colitis.

Figure 4A:
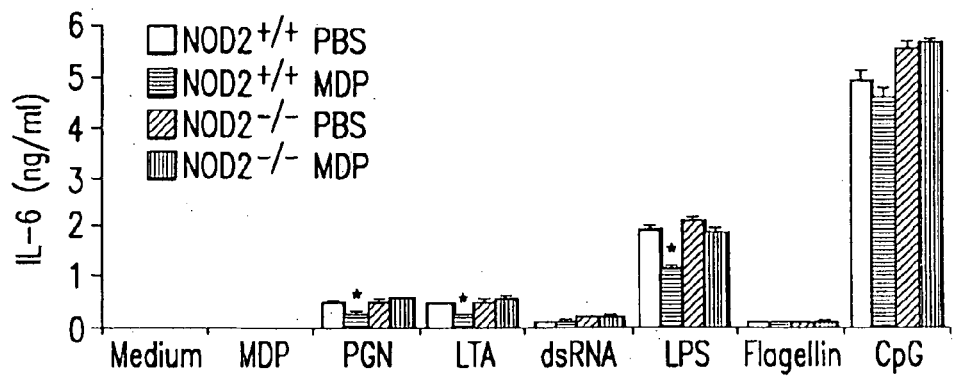
FIG. 4 shows cytokine production by MLN cells in mice treated with DSS. (A) MLN cells ($1\times10^6$/ml) isolated from NOD2$^{+/+}$ and NOD2$^{-/-}$ mice on day 5 were stimulated with broad range of TLR ligands. Culture supernatants were collected at 48 hrs and analyzed for cytokine production by ELISA. * P<0.05 when sups are compared with sups from mice treated with PBS (white bar). (B) Activation of NF-κB in MLN cells isolated from NOD2$^{+/+}$ and NOD2$^{-/-}$ mice on day 5 following stimulation with LPS or PGN. Nuclear extracts were prepared from MLN cells isolated from PBS or MDP-treated mice and stimulated with LPS or PGN for 2 hrs and then subjected to EMSA. (C) Nuclear extracts obtained in (B) assayed for p65 and c-Rel activation using NF-κB transcription factor ELISA. * P<0.05 compared to the nuclear extracts from PBS treated mice.
Figure 4A:
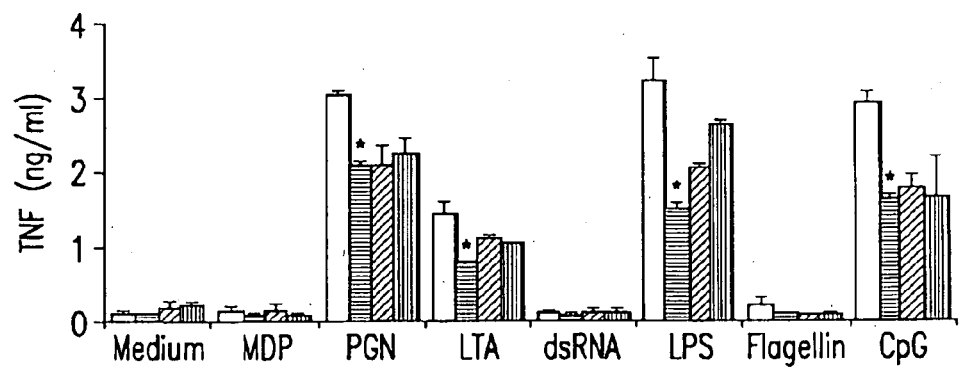
Figure 4B:
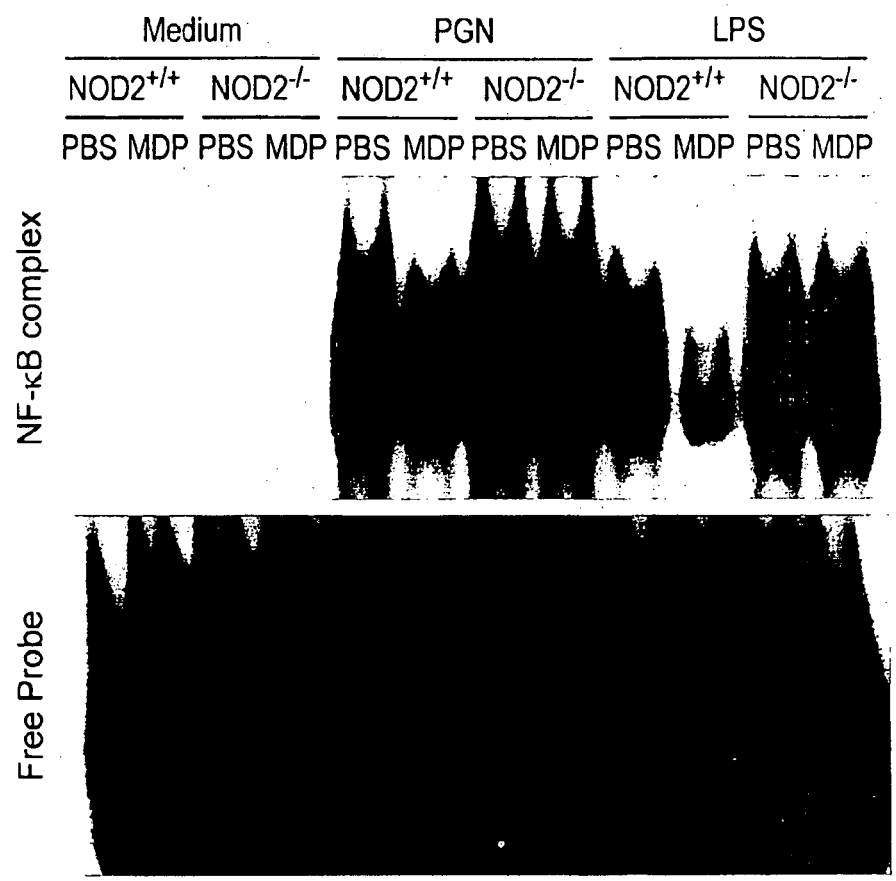

In studies of such protection, the profiles of cytokine production of mice described above that received MDP administration at the onset of DSS challenge were analyzed. For this purpose, MLN cells obtained from mice on day 5 after the initial challenge with DSS were stimulated with several TLR ligands. As shown in FIG. 4A, MDP administration was associated with a reduction in TLR2-, TLR3-, and TLR4-mediated IL-12p40, and IFN-γ production by MLN cells obtained from NOD2-intact, but not NOD2-deficient mice. However, this reduction of IL-12p40 or IFN-γ production seen in NOD2-intact mice treated with MDP was not observed in MLN cells from NOD2-deficient mice treated with MDP. Finally, as shown in EMSA and NF-κB ELISA study in FIGS. 4B and 4C respectively, PGN or LPS-mediated NF-κB activation was greatly suppressed in MLN cells from NOD2-intact mice treated with MDP as compared to those not so treated. Thus, as in the case of TNBS-colitis, MDP pre-treatment protects mice from DSS-induced colitis through down-regulation of pro-inflammatory cytokine responses evoked by a number of TLR ligands, not just TLR2.

Figure 5A:
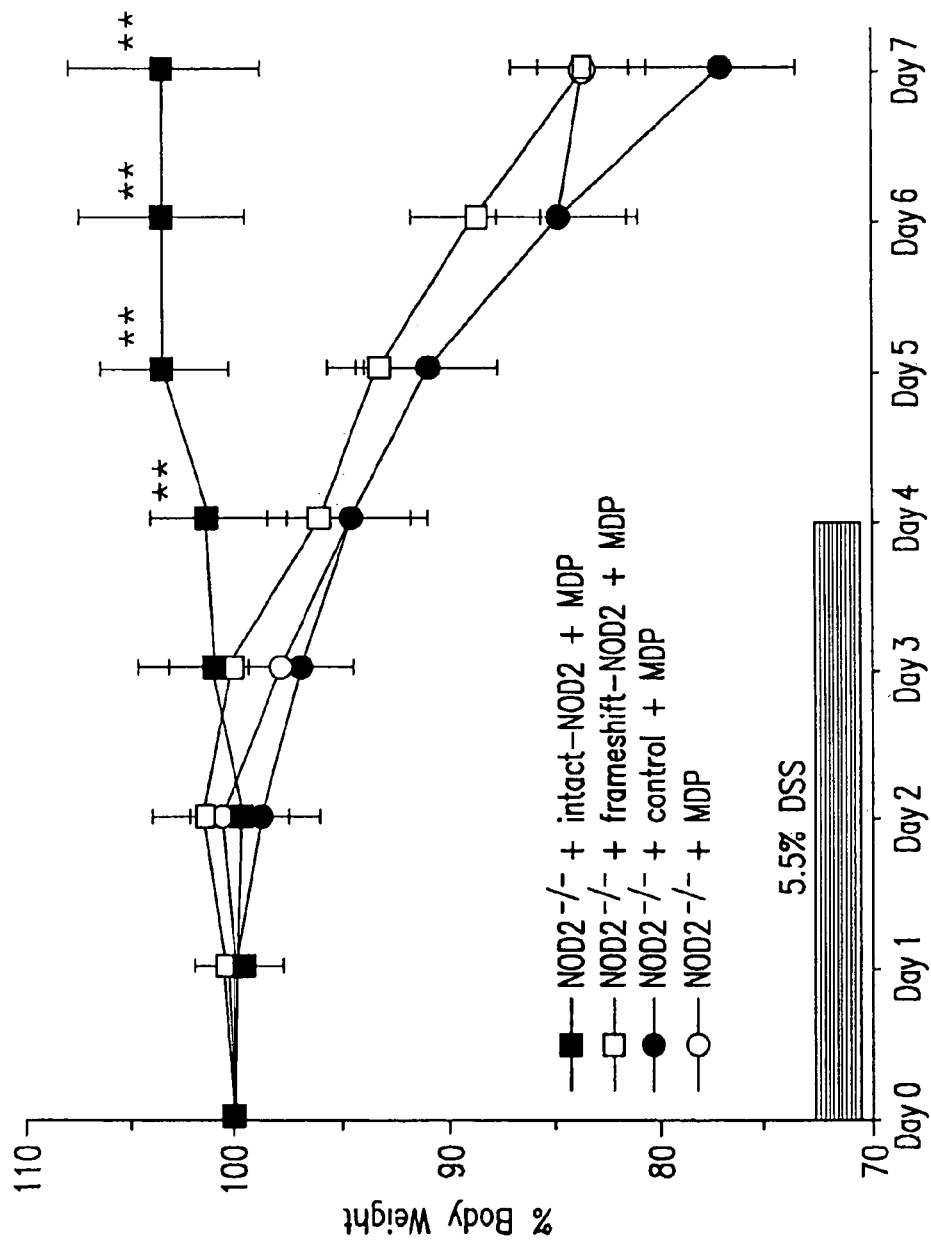
FIG. 5 shows DSS-colitis in MDP treated NOD2-deficient mice reconstituted with intact-, or frameshift-NOD2. NOD2-deficient (NOD2$^{-/-}$) mice were treated with drinking water containing 5.5% DSS for six days (Day 0-5). At an early phase of colitis induction (days 0, 1, 2), mice were administered MDP and HVJ-encapsulated plasmid (see Examples). (A) Changes of body weight in MDP administered NOD2-deficient mice reconstituted with intact-NOD2, frameshift-NOD2 or control empty vector. Weights of MDP administered NOD2-deficient mice given DSS are shown as a control. ** P<0.01 when time point values of intact-NOD2 reconstituted mice compared with control empty vector reconstituted mice. (B) H&E-stained colonic tissue of the mice harvested on day 7.
Figure 5B:
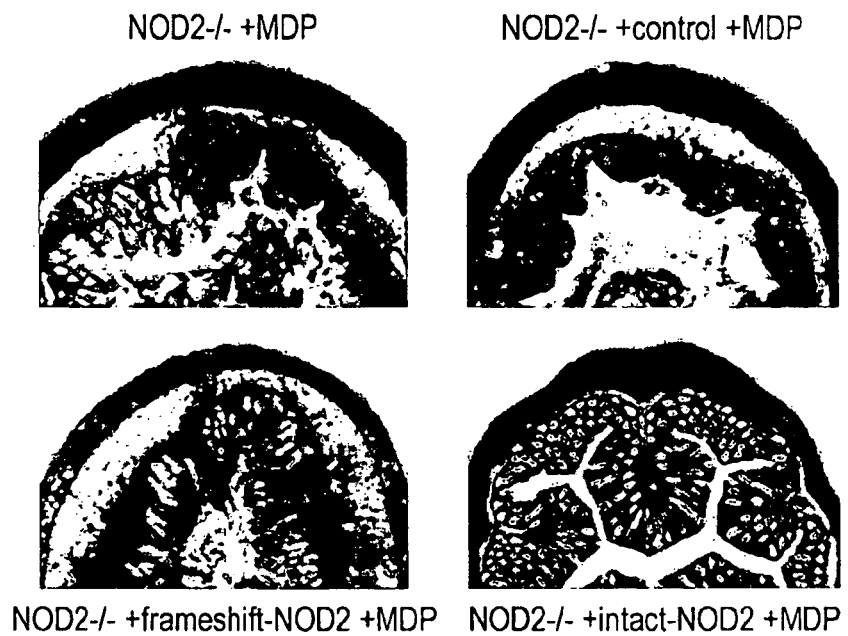

MDP Administration does not Protect Mice from DSS Colitis in Mice with Abnormal NOD2 Arising from a CARD15 Frame-shift Mutation The data above shows that MDP activation of NOD2 protects mice from TNBS or DSS colitis by down-regulating multiple TLR pathways. To relate these findings to Crohn's disease it was next determined whether NOD2 arising from a CARD15 mutation associated with Crohn's disease has a similar protective function. To this end, the ability of MDP to protect NOD2-deficient mice reconstituted with plasmids expressing murine intact CARD15, frame-shift CARD15 (L980fs) equivalent to human 3020insC or control "empty" plasmid from the development of DSS-colitis was determined. Accordingly, NOD2-deficient mice were treated with 5.5% DSS in the drinking water from day 0 to day 5 to induce the DSS-colitis. As in previous studies, the mice were administered MDP (100 µg IP) for three consecutive days beginning at the time of colitis induction (day 0, 1, 2), but in this case each MDP dose was accompanied by IP administration of either intact CARD15, frameshift CARD15 or control empty vector encapsulated in hemagglutinating virus of Japan (HVJ) for efficient in vivo delivery (21). As shown by the weight curves in FIG. 5A and the histologic data in FIG. 5B, while MDP injection protected NOD2-deficient mice reconstituted with intact CARD15 plasmid, it did not protect NOD2-deficient mice reconstituted with frame-shift CARD15 plasmid or with control empty plasmid. Colitis scores correlated with the tissue histology shown in FIG. 5B. Thus, these data show that abnormal NOD2 arising from the Crohn's-disease-associated CARD15 frame-shift mutation lacks the ability to control colonic inflammation upon systemic administration of MDP.

Human Dendritic Cells Subjected to Pre-activation of NOD2 by MDP Exhibit Reduced Pro-inflammatory Cytokine Production Upon Subsequent Stimulation with TLR Ligands Since MDP administration inhibits the inflammation occurring in murine models of colitis, it was of interest to determine the conditions under which MDP stimulation could also inhibit inflammatory cytokine responses to multiple TLR ligands in vitro.

In the relevant studies, the effect of MDP pre-stimulation of cells on the assumption that such pre-stimulation recapitulated the pre-treatment of mice in the above colitis models was determined. In initial studies, human monocyte-derived dendritic cells (DCs) were pre-incubated with medium (absence of NOD2 pre-stimulation) or with MDP (presence of NOD2 pre-stimulation) for 24 hours prior to stimulation with TLR ligands alone or stimulation with TLR ligands plus MDP (MDP co-stimulation). As shown in FIG. 6A, in keeping with prior results, in the absence of NOD2 pre-stimulation, PGN-mediated IL-12p40 and IL-6 production was inhibited by NOD2 co-stimulation, whereas dsRNA (double stranded RNA), LPS or CpG-mediated IL-12p40, IL-6, and TNF production was variably enhanced by NOD2 co-stimulation. In contrast, in the presence of MDP pre-stimulation, production of pro-inflammatory cytokines and chemokines such as IL-12p40, IL-6 and CXCL10 stimulated with a wide range of TLR ligands was inhibited and there was reversal of enhancement by NOD2 co-stimulation. The effect of NOD2 pre-stimulation and co-stimulation on TNF production was somewhat different since here NOD2 co-stimulation in the absence of NOD2 pre-stimulation was either associated with no inhibition or enhancement of TLR stimulation; nevertheless, in this case as well, such enhancement was usually reversed by NOD2 pre-stimulation. Thus, consistent with results obtained from studies of in vivo colitis models, MDP pre-treatment has a remarkable inhibitory effect on multiple types of TLR responses.

Figure 11B:
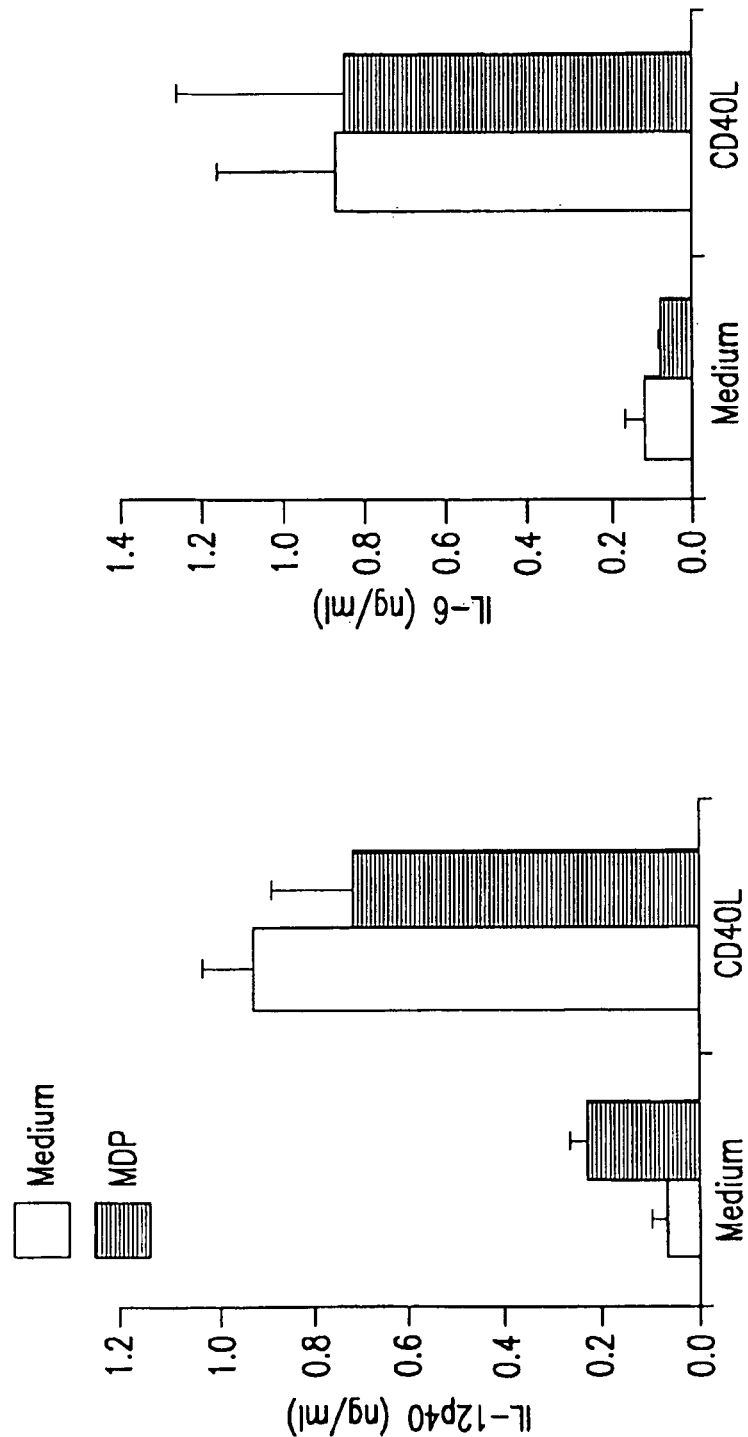
FIG. 11 shows that NOD2 pre-stimulation does not induce cell exhaustion or cell death. (A) IL-12p70, CXCL8, and IL-10 production by human DCs pre-incubated with MDP or medium and then stimulated with TLR ligands in combination with MDP as described in FIG. 6A. * P<0.05, ** P<0.01 when compared with the concentrations of cytokines produced by DCs pre-incubated with medium and stimulated with TLR ligands. (B) Production of IL-12p40 and IL-6 in human DCs pre-incubated with MDP or medium and then stimulated with CD40 ligands (10 μg/ml). (C) Human DCs stimulated with MDP or medium for 24 hrs were stained with FITC-conjugated Annexin V and propidium iodide (PI). The number in each quadrant shows the percentage of cells (top). PI-negative DCs were stained with FITC-conjugated anti-CD83, CD80, or CD86 Ab.
Figure 11C:
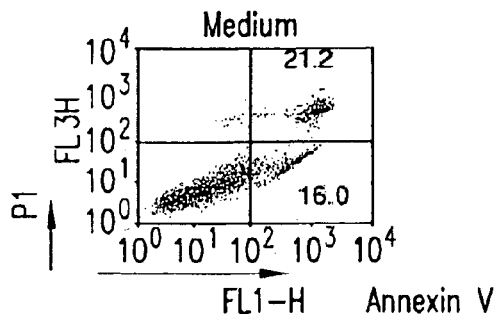
Figure 11C:
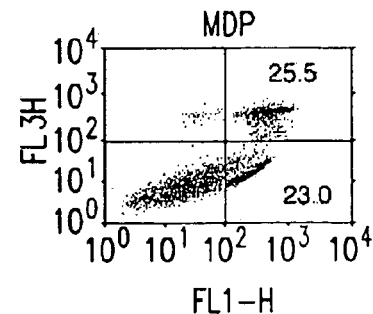
Figure 11C:
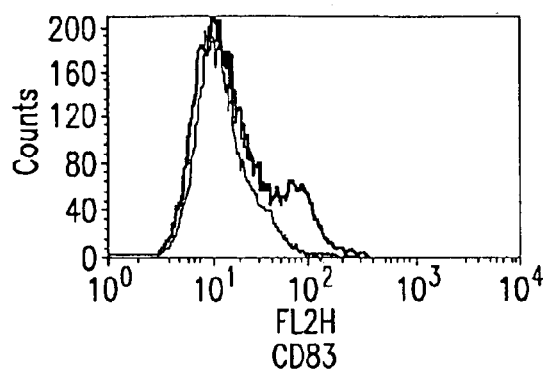
Figure 11C:
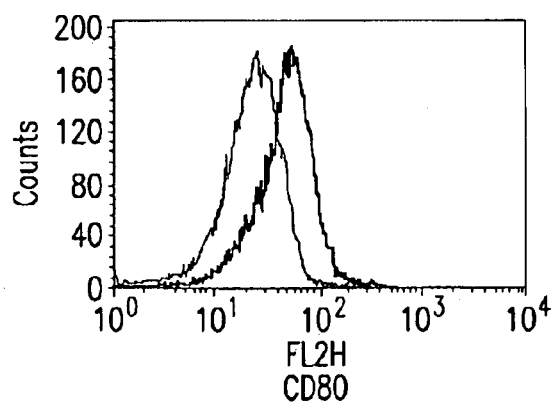
Figure 11C:
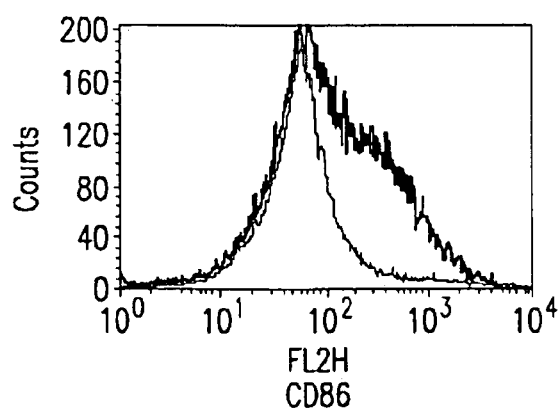

It is unlikely that the above inhibition of TLR responses by NOD2 pre-stimulation is due to induction of either cell "exhaustion" as defined previously (22) or simply to cell death. Thus, as shown in FIG. 6A, NOD2 pre-treatment had no inhibitory effect on either PGN- or LPS-induced TNF production and, as shown in FIG. 11A, no effect on CXCL8 (IL-8) production. In addition, as shown in FIG. 11B, pre-treatment had no effect on CD40 ligand-induced IL-12p40 or IL-6 production. As shown in FIG. 11C, pre-treatment led to enhanced expression of cell-activation markers without a marked increase of apoptotic cells. Finally, this reduction of pro-inflammatory cytokine production by NOD2 pre-stimulation was unlikely to be due to counter-regulation by IL-10 since, as shown in supplemental FIG. 1A, IL-10 production was also reduced in DCs subjected to NOD2 pre-stimulation.

Figure 12:
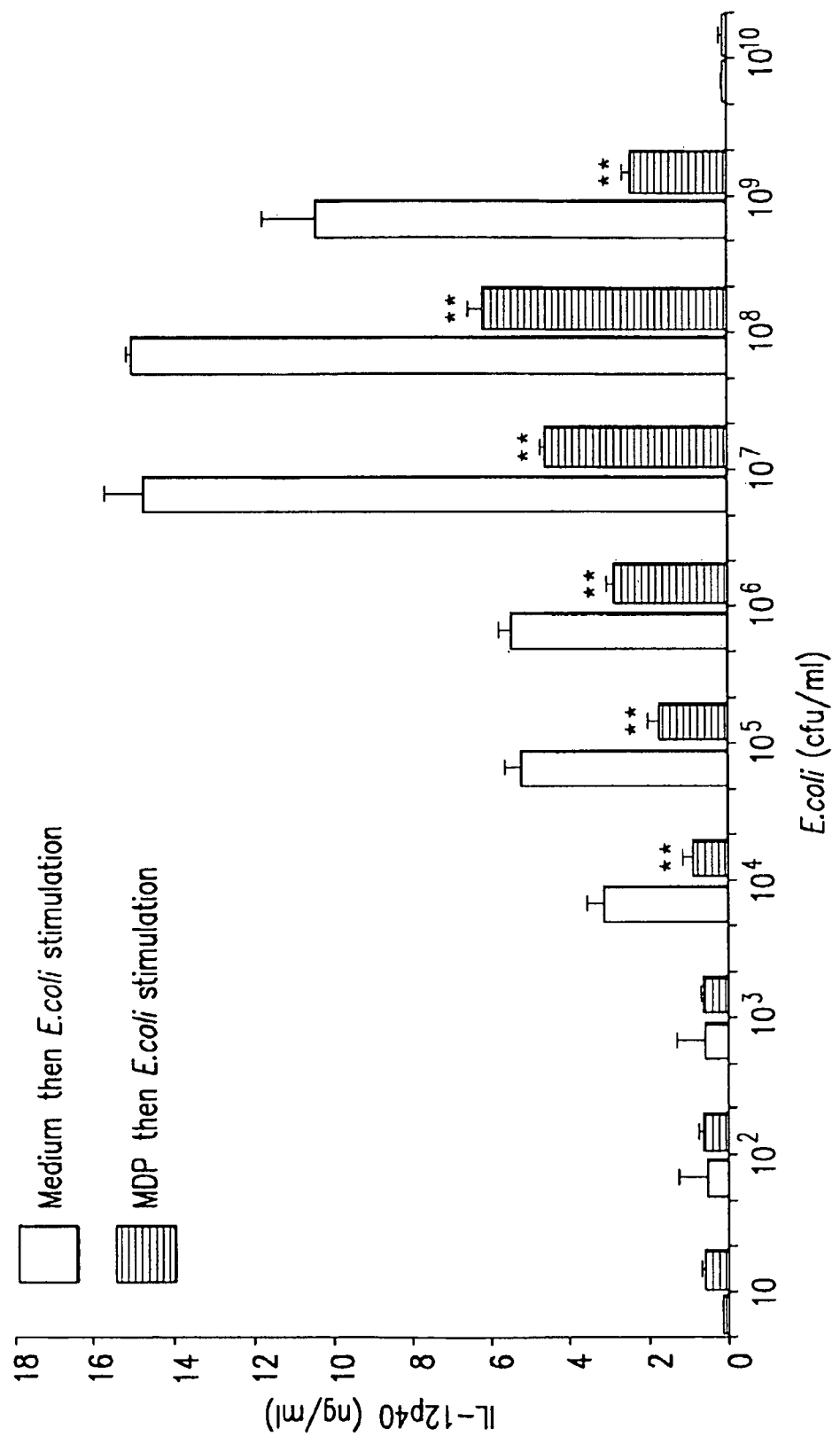
FIG. 12 shows that MDP pre-treatment suppresses the IL-12p40 production of human DCs in response to bacterial stimulation. Human DCs were pre-incubated with MDP or medium for 24 hrs and then stimulated with various concentrations of *E. coli*. Culture supernatants were collected at 24 hrs and analyzed for IL-12p40 production by ELISA. ** P<0.01 when compared with the concentrations of IL-12p40 produced by DCs pre-incubated with medium and stimulated with *E. coli*.

Taken together, these data show that NOD2 pre-stimulation reduces subsequent TLR-mediated induction of pro-inflammatory cytokines and chemokines even in situations where simultaneous TLR and NOD2 stimulation are associated with enhancing effects of NOD2 co-stimulation. In further proof of this conclusion, as shown in FIG. 12, DCs stimulated by killed *E. coli* organisms and by multiple TLR ligands simultaneously, also exhibited reduced IL-12p40 responses upon NOD2 pre-stimulation.

Figure 6B:
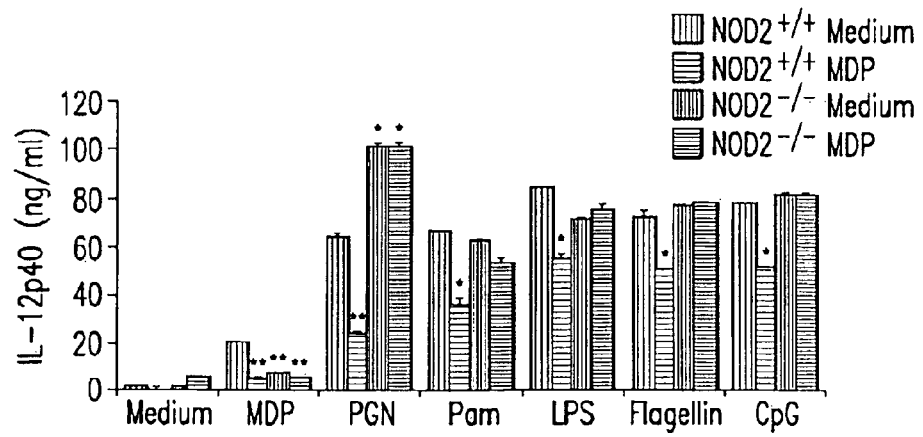
FIG. 6 shows human and mouse DCs pre-stimulated with MDP exhibit reduced cytokine and chemokine production when stimulated with TLR ligands. (A) Human monocyte-derived DCs ($1\times10^6$/ml) from six healthy donors were pre-incubated with MDP or medium for 24 hrs and then stimulated with broad range of TLR ligands alone or in combination with MDP for an additional 24 hrs. Culture supernatants were collected at 24 hrs and analyzed for cytokine and chemokine production by ELISA. * P<0.05, ** P<0.01 compared to sups from DCs pre-incubated with medium and stimulated with TLR ligands alone. (B) CD11c$^+$ DCs ($1\times10^6$/ml) derived from bone marrow cells from NOD2-intact (NOD2$^{+/+}$) and NOD2-deficient (NOD2$^{-/-}$) mice were pre-incubated with MDP (50 μg/ml) or medium alone for 24 hrs and stimulated with broad range of TLR ligands. Culture supernatants were collected at 24 hrs and analyzed for cytokine production by ELISA. * P<0.05, ** P<0.01 when sups are compared to NOD2-intact DCs pre-incubated with medium and stimulated with TLR ligands. (C) OVA$_{323-339}$ peptide-specific CD4$^+$ T cells (OT-II T cells) were purified from the spleen of OT-II transgenic mice; OT-II T cells ($1\times10^6$/ml) were co-cultured with NOD2-intact or NOD2-deficient BMDCs ($2\times10^6$/ml) in the presence of broad range of TLR ligands and OVA peptide (0.5 μM); culture supernatants were collected at 72 hrs and analyzed for IFN-γ production by ELISA. * P<0.05, ** P<0.01 compared to sups from NOD2-intact DCs pre-incubated with medium and stimulated with TLR ligands.

Murine Bone Marrow-derived DCs Also Exhibit Reduced TLR-mediated Cytokine Responses Upon NOD2 Pre-activation To both confirm and expand the above findings the effect of NOD2 pre-stimulation on bone marrow-derived DCs (BM-DCs) generated from NOD2-deficient mice was determined. In these studies, BMDCs pre-incubated with MDP for 24 hours were subjected to stimulation with broad range of TLR ligands. As shown in FIG. 6B, NOD2 pre-stimulation led to a substantial reduction of IL-12p40 and IL-6 production by NOD2-intact BMDCs stimulated with TLR2, TLR4, TLR5, and TLR9 ligands. In contrast, this inhibitory effect was not observed with NOD2-deficient BMDCs. As shown in FIG. 13A a similar effect of MDP pre-treatment was observed with IL-12p70 and TNF production. Finally, as shown in FIG. 13B, MDP stimulation did not affect BMDC expression of co-stimulatory molecules or MHC class II expression. Similarly, MDP treatment did not change BMDC expression of TLR2 and TLR4.

Figure 6C:
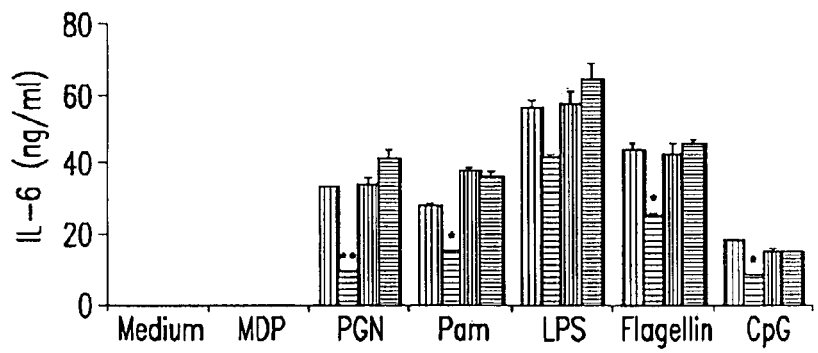
Figure 6C:
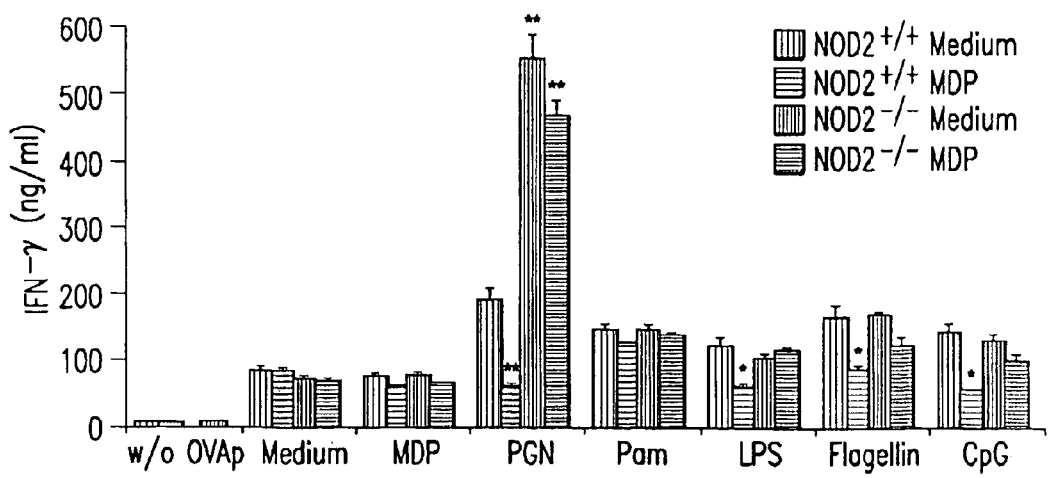

In further studies, whether this reduction of pro-inflammatory cytokine responses by NOD2 pre-stimulation results in decreased cytokine responses by naïve ovalbumin (OVA)-specific CD4$^+$ T cells was determined. For this purpose the ability of DCs subjected to NOD2 pre-stimulation to induce OVA-specific T cells to produce IFN-γ upon co-culture with OVA-peptide and naïve T cells from OVA-T cell receptor transgenic (OT-II) mice was assessed. As shown in FIG. 6C, OVA-peptide presentation by NOD2-intact NOD2-pre-stimulated BMDCs as compared to non-pre-stimulated BMDCs led to greatly reduced IFN-γ production by CD4$^+$ T cells isolated from the spleen of OT-II transgenic mice in the presence of TLR2, TLR4, TLR5, and TLR9 ligands. In contrast, this reduced response was not observed with MDP pre-stimulated NOD2-deficient BMDCs. These studies of mouse DCs thus confirm the inhibitory effect of NOD2 pre-stimulation observed with human DCs and provide evidence that the effect is in fact mediated by NOD2.

Inhibition of TLR Cytokine Responses by NOD2 Pre-Stimulation is Associated with Up-regulation of IRF4

Figure 7A:
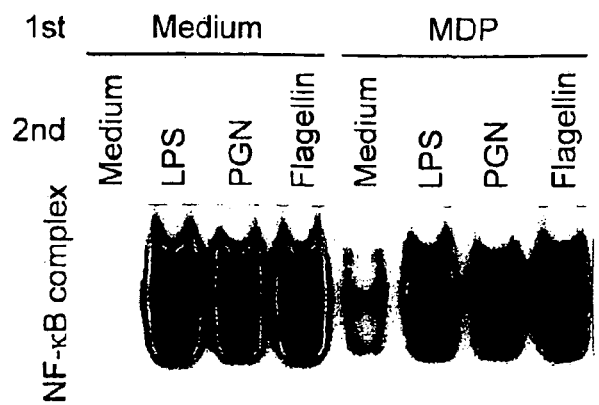
FIG. 7 shows that NOD2 stimulation is associated with up-regulation of IRF4 expression. (A) NF-κB activation in human monocyte-derived DCs. DCs were pre-incubated with MDP or medium for 24 hrs and then stimulated with LPS, PGN, or flagellin for 2 hrs; nuclear extracts of the cells were then obtained and subjected to gel-shift assays; results shown representative of those obtained with two healthy donors. (B) Up-regulation of IRF4 in MDP stimulated human monocyte-derived DCs. Whole cell extracts prepared from DCs incubated with MDP, LPS or medium for 24 hrs were immunoblotted with antibodies to the indicated components; results shown representative of those obtained in three healthy donors. (C) IRF4 expression in monocyte-derived DCs transfected with IRF4 siRNA. DCs were transfected with 2 μg of IRF4 siRNA, IRAK-M siRNA or control siRNA using the Amaxa nucleofection method; 16 hrs after the transfection, DCs were stimulated with MDP, LPS or medium for 24 hrs at which point whole cell extracts were prepared and subjected to immunoblotting with antibodies to the indicated components. (D) Effects of IRF4 or IRAK-M siRNA transfection on cytokine production by human monocyte-derived DCs. DCs ($2\times10^7$/ml) from six healthy donors were transfected with IRF4 siRNA, IRAK-M siRNA or control siRNA as described in C. After 24 hrs of culture with MDP, LPS or medium, DCs were stimulated with PGN, Pam3CSK4 or LPS for another 24 hrs; culture supernatants were assayed for IL-12p40 by ELISA. * P<0.05, ** P<0.01 when compared to DCs transfected with control siRNA and pre-incubated with medium (white bar).

The fact that multiple TLR responses could be inhibited with NOD2 pre-stimulation allowed exploration of the molecular basis of the inhibitory effect. Initially, the effect of MDP pre-stimulation on subsequent TLR activation of NF-κB in human DCs was determined by performing gel-shift assays on nuclear extracts isolated from the stimulated DCs. As shown in FIG. 7A, nuclear extracts isolated from MDP-pre-stimulated DCs subsequently stimulated with LPS, PGN, or flagellin gave rise to bands of reduced intensity when incubated with $^{32}$P-labelled oligo probes specific to NF-κB as compared to extracts from cells not subjected to pre-stimulation. These data show that NOD2 pre-stimulation can reduce subsequent activation of NF-κB by TLR ligands.

Figure 7B:
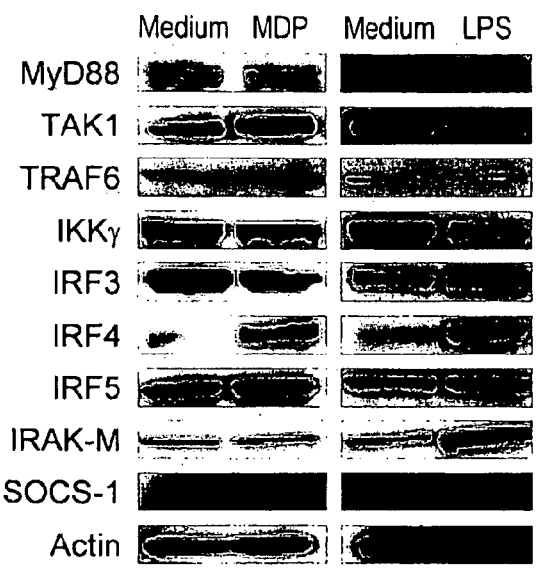
Figure 14A:
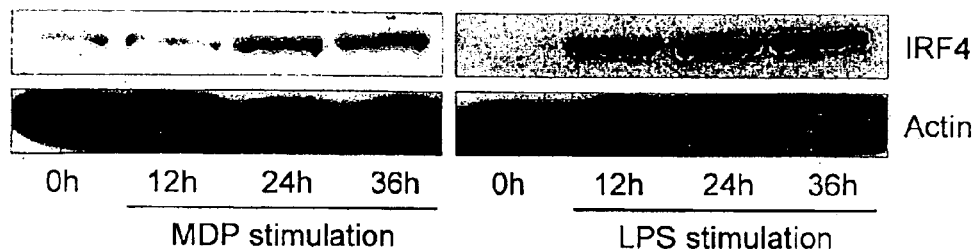
FIG. 14 shows that silencing of IRF4 with IRF4-siRNA reverses MDP-mediated suppression. (A) Human DCs were stimulated with either MDP (10 μg/ml) or LPS (1 μg/ml). Cell lysates were collected at the indicated time points and IRF4 expression was assessed by immunoblot. (B) Human DCs were transfected with either control scrambled siRNA or two different IRF4-specific siRNA (2 μg). After transfection, cells were washed and either left alone or pre-stimulated with MDP for 24 hrs, and then stimulated with either PGN (10 μg/ml) or LPS (1 μg/ml) after washing. Culture supernatants were collected at 24 hrs and analyzed for IL-12p40 production by ELISA. ** P<0.01 when compared with the concentrations of cytokines by DCs transfected with control siRNA and pre-incubated with medium (white bar).

In further studies immunoblot analyses were performed to determine the expression of signaling molecules involved in the TLR signaling pathway or those previously shown to be negative regulators of that pathway (19, 20, 23) in cells incubated in medium vs. cells incubated with MDP or LPS. Because of the results of the gel-shift assay described above, the focus was on those molecules involved in the activation of NF-κB. As shown in FIG. 7B, there was no difference in the expression of TLR signaling molecules such as MyD88, TAK1, TRAF6, IRF3, IRF5 or IKK-γ in cells without and with either NOD2 (MDP) or TLR4 (LPS) stimulation. In contrast, MDP-stimulated cells expressed increased amounts of the negative regulator IRF4 at 24 hours after stimulation (and, as shown in FIG. 14A, at 36 hours as well) but not other negative regulators such as IRAK-M or SOCS-1. Consistent with previous reports (19, 20) (23, 24), cells stimulated by LPS expressed increased amounts of both IRF4 and IRAK-M, but not SOCS-1.

Inhibition of TLR Cytokine Responses by NOD2 Pre-Stimulation Requires the Expression of IRF4

Figure 7C:
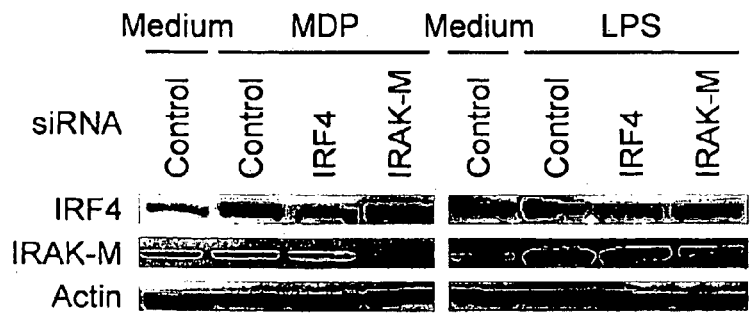
Figure 14B:
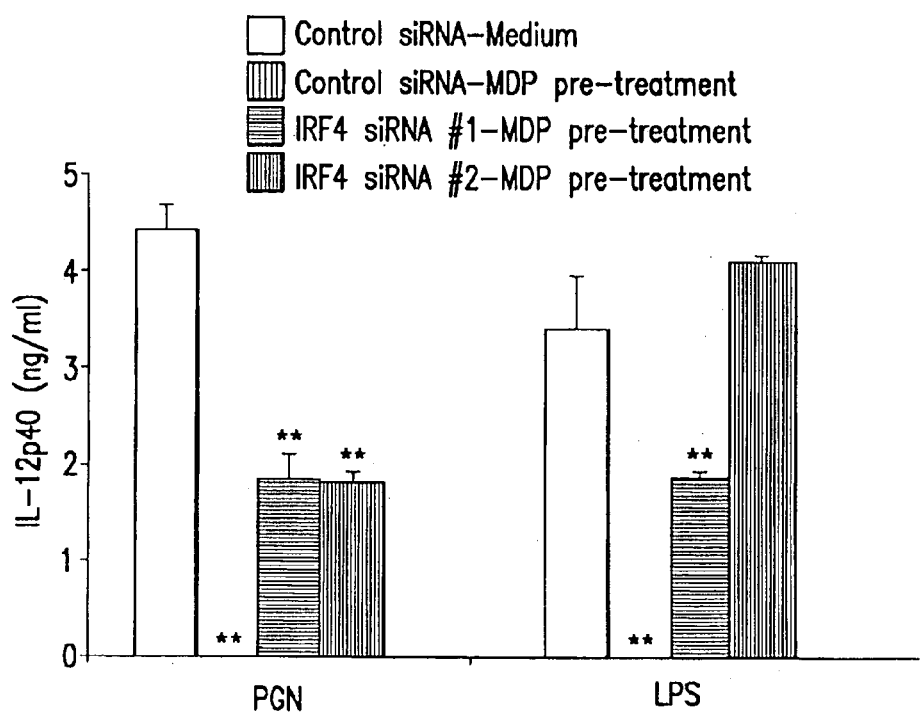

To determine that NOD2 pre-stimulation is not only associated with IRF4 expression but actually requires IRF4 expression, studies were conducted to determine whether gene silencing of IRF4 or IRAK-M expression by siRNA specific for these molecules affects NOD2- or TLR4-mediated inhibitory effects. As shown in FIG. 7C, transfection of human DCs with a mixture of IRF4 siRNA substantially reduced expression of IRF4 at the protein level in MDP- and LPS-stimulated human DCs. Similarly, transfection of IRAK-M siRNA reduced expression of IRAK-M in LPS-stimulated cells. As shown in FIG. 7D (top), transfection of IRF4 siRNA, but not IRAK-M siRNA led to increased IL-12p40 production in MDP-pre-stimulated DCs subsequently stimulated with PGN, Pam$_3$CSK4, and LPS. In addition, as shown in FIG. 7D (bottom), transfection of IRAK-M siRNA, but not IRF4 siRNA led to increased IL-12p40 production in LPS-pre-incubated DCs stimulated with PGN, Pam$_3$CSK4, and LPS. In a final study, whether individual IRF4-specific siRNAs could abolish inhibition of NOD2 pre-stimulation to rule out off-target effects of the siRNA mixture was determined. As seen in the studies shown in FIG. 14B, addition of two different siRNAs again led to loss of the inhibition of NOD2 pre-stimulation, in both PGN- and LPS-stimulated cell cultures.

Figure 8A:
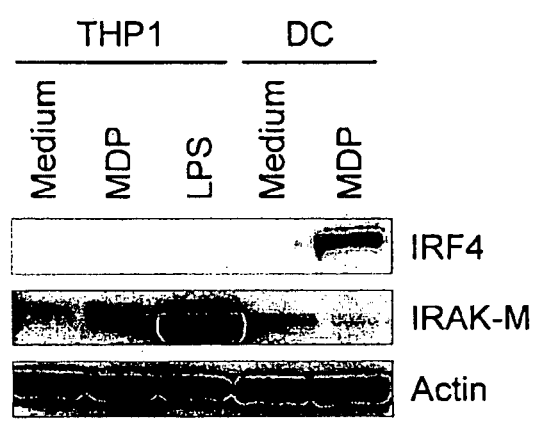
FIG. 8 shows NOD2-induced IRF4 inhibition of TLR signaling. (A) Whole cell extracts were prepared from THP1 cells stimulated with MDP or LPS for 24 hrs and then immuno-blotted with antibodies to IRF4, IRAK-M and actin. (B) THP1 cells ($5\times10^5$/ml) were pre-stimulated with MDP, LPS or medium for 24 hrs and stimulated with TLR ligands; culture supernatants were collected at 24 hrs and analyzed for cytokine production by ELISA. * P<0.05 when compared with the concentrations of cytokines by cells pre-incubated with medium and stimulated with TLR ligands (white bar). (C) Physical interactions between IRF4 and RICK, MyD88, TRAF6. Whole cell extracts of HEK293 cells transfected with vectors (2 μg) expressing FLAG-tagged human IRF4 and HA-tagged human MyD88 or with untagged RICK, TRAF6, TRAF2 were immuno-precipitated with anti-FLAG conjugated beads and then immunoblotted with anti-HA antibody or with anti-RICK, TRAF6, or TRAF2. (D) Negative regulation of NF-κB by IRF4. HT-29 cells ($1\times10^5$/96 well plate) transfected with pNF-κB-Luc (50 ng) and pSV-β-galactosidase (10 ng) were co-transfected with vectors expressing human RICK (200 ng), human MyD88 (200 ng) or human TRAF6 (200 ng) with or without an IRF4 expressing vector (50 ng, 200 ng, 1000 ng). *P<0.05, ** P<0.01 when compared to cells without IRF4 transfection (white bar). (E) Physical interaction of IRF4 and RICK in MDP pre-stimulated human DCs. DCs were cultured with MDP or medium for 24 hrs and then stimulated with Pam$_3$CSK4 for an additional hour; whole cell extracts were prepared and then immuno-precipitated with anti-IRF4 Ab and immunoblotted with anti-RICK Ab.
Figure 15A:
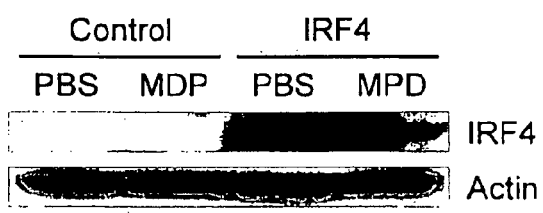
FIG. 15 shows that susceptibility to MDP suppression is restored by IRF4 reconstitution. THP1 cells were transfected with a vector expressing FLAG-tagged human IRF4 or a control vector (1 μg) by the Amaxa nucleofection method; the cells were then pre-incubated with medium or MDP for 24 hrs and then stimulated with PGN, Pam3CSK4, and LPS. Expression of IRF4 was analyzed 48 hrs after the transfection by immuno-blotting with anti-FLAG Ab (top); culture supernatants were collected at 24 hrs and analyzed for cytokine production by ELISA (bottom). * P<0.05, ** P<0.01 when compared with the concentrations of cytokines by cells transfected with a control vector and preincubated with medium (white bar).
Figure 15B:
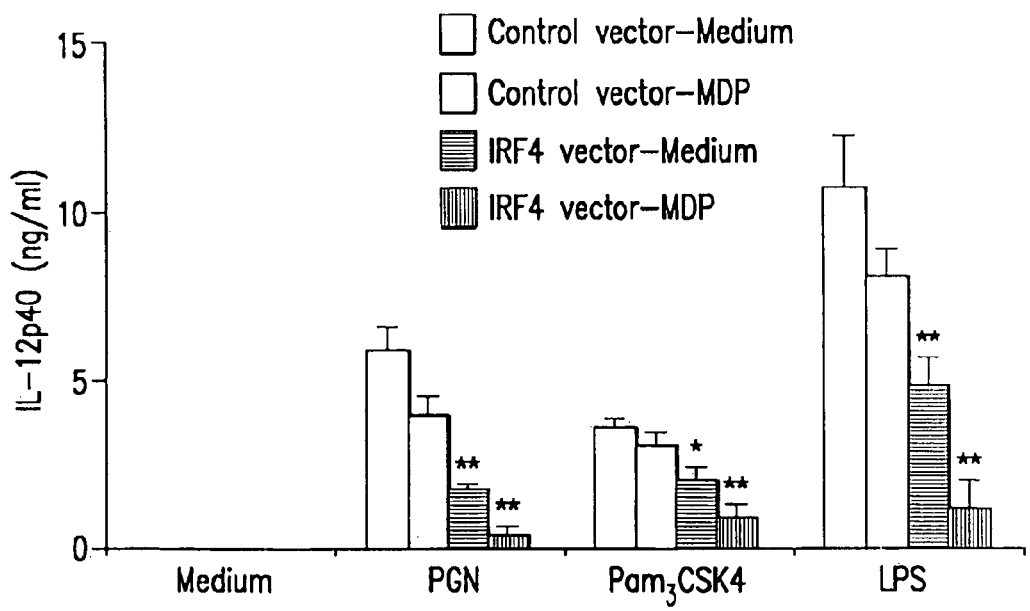

In another approach to study the role of IRF4 in inhibition following NOD2 pre-stimulation, the capacity of such pre-stimulation to inhibit responses in cells naturally lacking IRF4 such as human monocytes (25) was determined. In these studies whether or not NOD2 pre-stimulation of THP1 cells, a monocytic cell line, affects their subsequent TLR-induced cytokine production was determined. As shown previously, THP1 cells express NOD2 (26, 27), but, as shown in FIG. 8A, do not express IRF4 before or after stimulation by MDP or LPS; in contrast, they express IRAK-M, especially after stimulation with LPS. As shown in FIG. 8B, in keeping with the data shown above, MDP pre-stimulation of THP1 cells did not result in reduced IL-12p40 or TNF responses following subsequent stimulation with PGN, Pam$_3$CSK4 or LPS whereas LPS pre-stimulation did lead to reduced IL-12p40 or TNF production by THP1 cells subsequently stimulated with PGN or LPS. Finally, as shown in FIG. 15, transfection of THP1 cells with an IRF4-expressing vector led to down-regulation of PGN, Pam$_3$CSK4 and LPS responses which was particularly evident after MDP pre-stimulation; thus, the lack of response to MDP pre-stimulation could in fact be shown to be due to lack of IRF4 expression.

Along similar lines whether NOD2 pre-stimulation affected TLR-induced CXCL8 or CXCL10 production in HT-29 cells (i.e., a highly differentiated epithelial cell line) which like THP1 cells do not express IRF4 was determined. Here again, NOD2 pre-stimulation did not down-regulate responses to subsequent stimulation with dsRNA or flagellin stimulation.

The above in vitro studies involving gene silencing of IRF4 and the study of cells naturally lacking IRF4 provide strong support that the inhibitory effects of NOD2 pre-stimulation depend on IRF4. Further support for this view comes from in vivo studies described below.

Sensitivity of PGN and LPS Signaling to IRF4 Inhibition

Figure 16A:
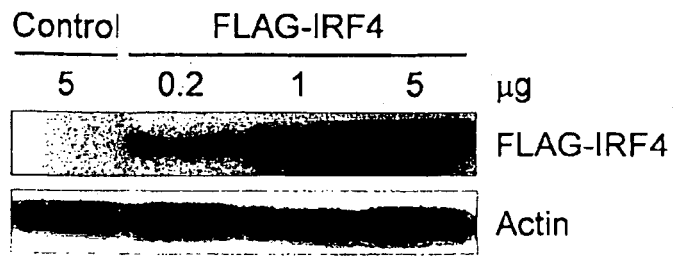
FIG. 16 shows that PGN-signaling is more sensitive to IRF4-mediated suppression than LPS-signaling. Expression of transfected IRF4 in human DCs (top); DCs prepared from three healthy donors were transfected with various doses of FLAG-tagged IRF4 cDNA; whole cell extract were prepared 24 hrs after transfection followed by immuno-blotting. IL-12p40 (middle) and IL6 (bottom) production by IRF4 transfected DCs; after transfection, cells were stimulated with PGN or LPS for 24 hrs. Culture supernatants were analyzed for cytokine production by ELISA. * P<0.05, ** P<0.01, compared to control vector-transfected cells.
Figure 16B:
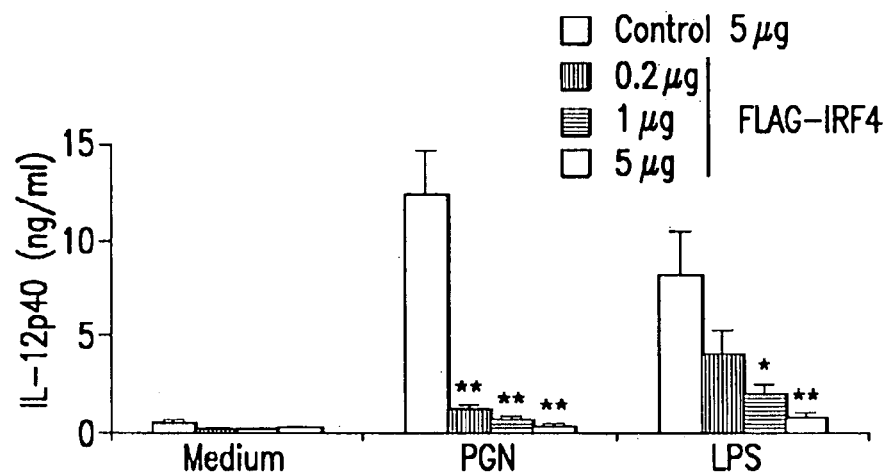
Figure 16C:
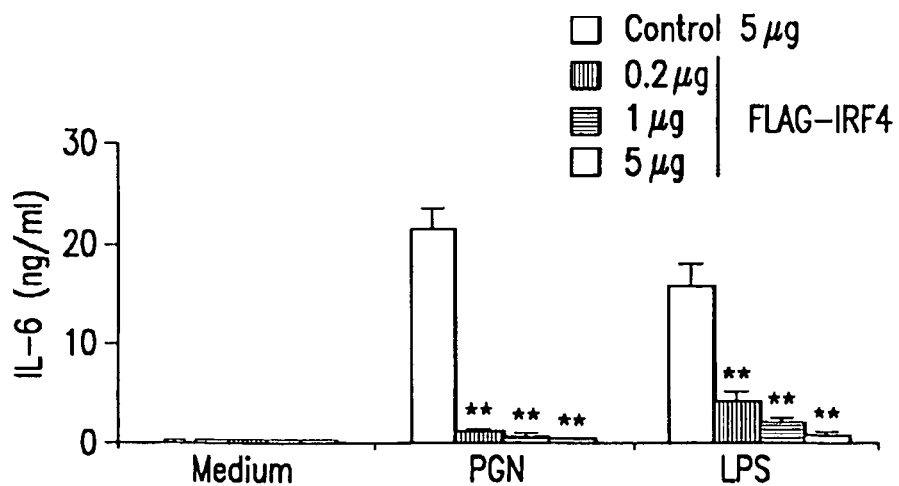

The studies described above provided data showing that PGN and LPS responses differed in their sensitivity to IRF4-mediated inhibition; NOD2 pre-stimulation produced more profound inhibition of PGN (TLR2) responses than LPS (TLR4) responses and suppression of PGN-mediated IL-12p40 production was more resistant to IRF4 siRNA-induced reversal than that of LPS-mediated IL-12p40 production (FIG. 7D). To examine this possibility more directly, PGN and LPS responses in human DCs transfected with increasing doses of FLAG-tagged IRF4 cDNA (28) were examined. As shown in FIG. 16 (top), transfection of FLAG-tagged IRF4 induces protein expression in a dose-dependent manner. In addition, as also shown in FIG. 16 (middle and bottom), low expression of transfected IRF4 (0.2 µg) is sufficient to greatly inhibit PGN-induced production of IL-12p40 and IL-6 whereas, in contrast, high expression of IRF4 is necessary to comparably inhibit LPS-induced production of these cytokines. Thus, PGN-mediated TLR2 signaling is more sensitive to negative regulation by IRF4 than LPS-mediated TLR4 signaling. Since IRF4 levels can be assumed to be low in the absence of pre-stimulation, i.e., when cells are stimulated by TLR ligands and MDP simultaneously, these findings explain why simultaneous stimulation of TLR ligands and MDP results in reduced PGN-induced production of IL-12p40 whereas it has little effect on IL-12p40 production by other TLR ligands (11).

NOD2-induced IRF4 Inhibition of TLR Signaling

Figures 8C, 8D, 8E:
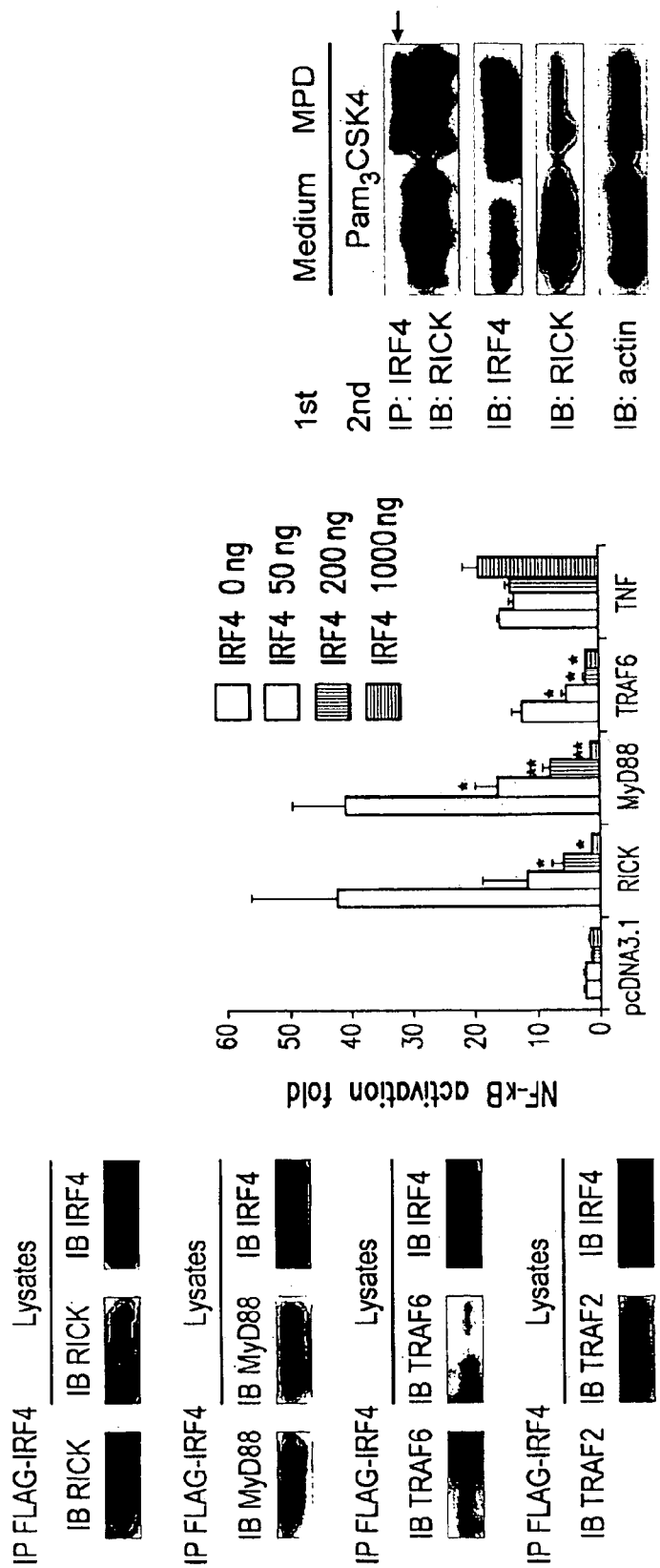

In further studies of NOD2-induced inhibition of TLR signaling were explored. In initial studies the possible physical interactions between IRF4 and various components of the TLR signaling pathway were determined. To this end, immunoblots were performed on extracts of human embryonic kidney (HEK) 293 cells transfected with FLAG-tagged human IRF4 cDNA (28) together with MyD88, TRAF6 or RICK cDNA, relevant components of the TLR and NOD2 signaling pathways. In addition to these molecules, TRAF2, which is a component of TNF signaling pathway, was also transfected together with IRF4 as a negative control. As shown in FIG. 8C, it was found that each of these components, except for TRAF2, does indeed bind to IRF4.

In further studies, plasmids expressing MyD88, TRAF6, RICK, and IRF4 were co-transfected into HT-29 colon epithelial cells expressing an NF-κB luciferase vector to determine the capacity of IRF4 to inhibit the capacity of each of the components to activate the vector and its generation of luciferase. As shown in FIG. 8D, co-transfection of IRF4 led to a dramatic dose-dependent reduction in NF-κB activation by each of the components, whereas IRF4 had no effect on the ability of TNF, a non-TLR/NLR-related NF-κB activator to activate NF-κB that signals mainly through TRAF2, shown above not to interact with IRF4. These overexpression studies therefore suggest that IRF4 acts as a negative regulator of NF-κB activation by binding to and thereby impeding the activity one of the components of the TLR activation pathway. In additional studies, extracts of stimulated human DCs (i.e., cells in which IRF4 and signaling components were not over-expressed) were subjected to immunoprecipitation and immunoblotting with available antibodies. As shown in FIG. 8E, extracts of NOD2 pre-stimulated cells but not medium-pre-stimulated cells subsequently stimulated with Pam$_3$CSK4 contained RICK bound to IRF4 suggesting that the inhibiting effects of NOD2 signaling is mediated by this complex.

Systemic Administration of MDP Prevents the Development of TNBS- or DSS-colitis by Up-regulating IRF4 Expression The in vitro studies described above provided considerable evidence that the suppression of multiple TLR pathways mediated by MDP activation of NOD2 depends upon the expression of IRF4. To verify this hypothesis in vivo, studies of the effect of MDP pre-treatment on the development of experimental colitis to determine if IRF4 also mediated inhibitory MDP effects in these models were conducted.

Figure 9A:
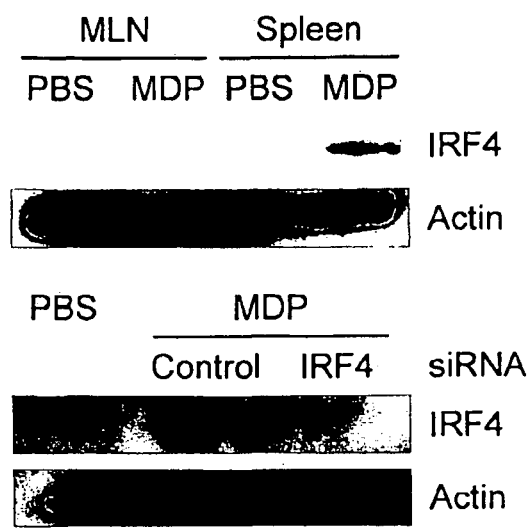
FIG. 9 shows that systemic administration of MDP prevents the development of TNBS-colitis by up-regulating IRF4 expression. Mice administered intra-rectal TNBS on day 0 were injected MDP or PBS i.p. on days −3, −2, −1 and also administered 100 μg of HVJ-encapsulated control siRNA or IRF4 siRNA by intra-rectal instillation on days −2, −1, 0, 1. (A) IRF4 expression in CD11b$^+$ myeloid cells from the MLNs and spleen from mice on day 0 (top); IRF4 expression in whole cell extracts of CD11b$^+$ myeloid cells from MLNs isolated from mice treated with IRF4-siRNA on day 0 (bottom). (B) Changes of body weight in mice treated with MDP and siRNAs. ** P<0.01 when compared with body weight of mice treated with PBS. (C) H&E-stained colonic tissue of the mice harvested on day 4. Histology of PBS-treated mice and IRF4-siRNA-treated mice showed massive infiltration of mononuclear cells as well as destruction of crypt architecture; histology of control siRNA-treated mice showed almost normal colon tissue with minimal infiltration of mononuclear cells. (D) MLN cells ($1\times10^6$/ml) isolated from the mice on day 4 were stimulated with broad range of TLR ligands; culture supernatants were collected at 48 hrs and analyzed for cytokine production by ELISA. * P<0.05, ** P<0.01 when compared with the concentrations of cytokines from PBS-treated mice (open bar).
Figure 9B:
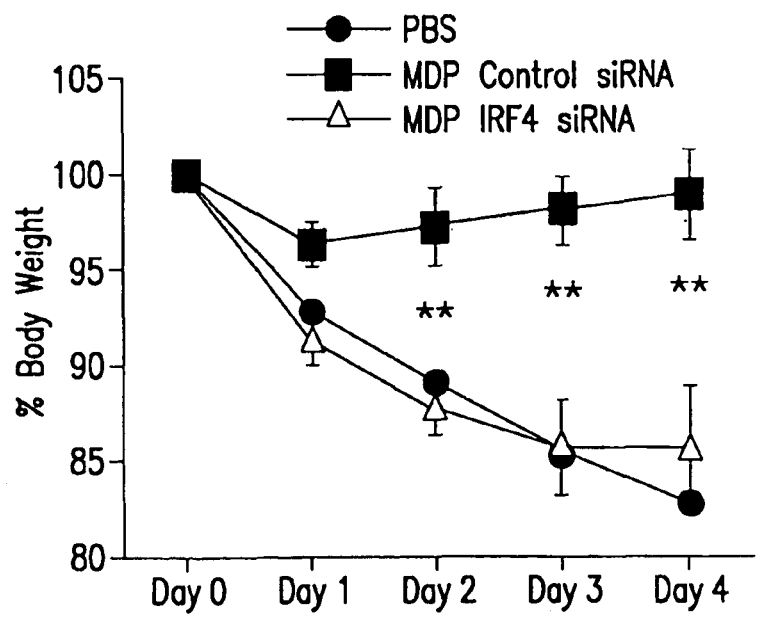
Figure 9C:
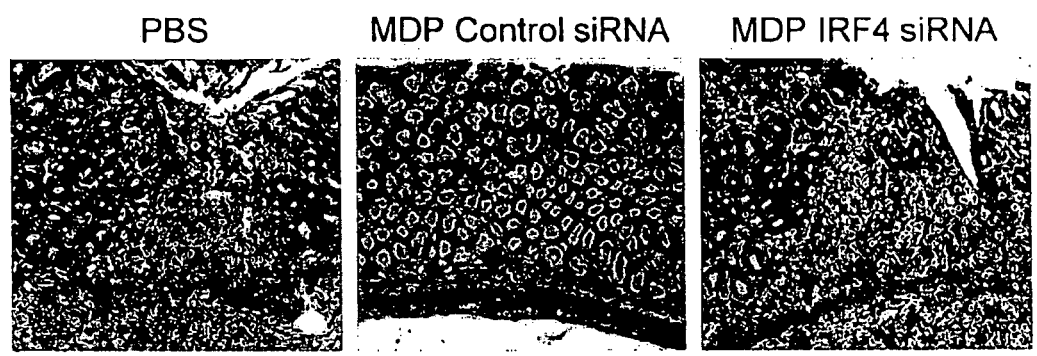

It was first determined whether systemic injection of MDP induces up-regulation of IRF4 as in the case of human DCs. For this, CD11b$^+$ myeloid cells were isolated from MLNs and spleens of mice that had been administered either MDP or PBS. As shown in FIG. 9A (top), IRF4 protein was barely detectable in cells from PBS-treated mice but was easily detected in cells from MDP-treated mice. The effect of IRF4 gene-silencing on the capacity of MDP administration to protect mice from TNBS-colitis was determined next. In these studies, mice administered MDP (IP) according to the schedule described in FIG. 1 were also administered 100 µg of either siRNA targeting murine IRF4 or control siRNA encapsulated in hemagglutinating virus of Japan (HVJ) by the intra-rectal route on day −2 to day 1 (with respect to TNBS administration). As shown in FIG. 9A (bottom), induction of IRF4 expression was not seen in CD11b$^+$ MLN cells examined on day 0 obtained from mice administered both MDP and HVJ-IRF4 siRNA whereas IRF4 expression was clearly seen in cells from mice administered MDP and HVJ-control siRNA. As shown in FIG. 9B, while mice administered MDP and control siRNA did not exhibit body weight loss following TNBS challenge, mice administered MDP and IRF4 siRNA exhibited a body weight loss similar to that of mice administered PBS. As shown in FIG. 9C, these weight loss data correlated with pathology: mice administered MDP and IRF4 siRNA exhibited severe colonic epithelial cell damage and massive infiltration of inflammatory cells in the LP equivalent to the changes seen in mice treated with PBS. Finally, as shown in FIG. 9D, the weight loss data correlated with cytokine production findings in that the marked reduction in TLR-mediated IL-12p40, IL-6, and TNF accompanying MDP-administration was almost completely restored by IRF4 siRNA administration. Taken together, these data show that MDP administration protects mice from TNBS-colitis via its ability to induce NOD2-induction of IRF4 and subsequent IRF4-inhibition of TLRs-mediated inflammatory cytokine production.

Finally, it was determined whether the protection from DSS-colitis in mice treated with MDP depends upon IRF4, in this case utilizing a well-described gene-targeted mouse with a background strain susceptible to DSS-colitis (29). Indeed, immunoblot studies of extracts of spleen cells of IRF4-deficient mice with DSS-colitis did not give an IRF4 band whereas IRF4-intact mice did give a band. As shown in FIG. 10A, as judged by body weight loss, MDP administration as described above did not inhibit the development of DSS-colitis in IRF4-deficient mice whereas it did inhibit such colitis in IRF4-intact mice. In addition, as shown in FIG. 10B, the colitis scores of MDP-treated and untreated IRF4-deficient mice were not significantly different whereas MDP-treated IRF4-intact mice were significantly reduced as compared to untreated IRF4-intact mice. Finally, as shown in FIG. 10C, whereas MLN cells from MDP-treated IRF4-intact mice exhibited a clear decrease in both IL-12p40 and IFN-γ secretion upon TLR ligand stimulation, comparable cells from IRF4-deficient mice exhibited no such decrease.

The present invention shows that MDP signaling via NOD2 has, surprisingly, much more global inhibitory effects in that when initiated prior to the induction of the TLR responses it inhibits not only TLR2 and IL-12, but also other TLR responses and other cytokine responses both in vivo and in vitro. This conclusion is based on the first in vivo studies that showed that administration of MDP to mice led to the amelioration of both DSS-colitis and the hapten (TNBS)-induced colitis and that, furthermore, such amelioration was associated with the down-regulation of mucosal innate responses involving multiple TLR pathways. It was also based on in vitro studies that showed first that NOD2 (MDP) pre-stimulation of human monocyte-derived DCs is followed by a greatly diminished capacity of TLR2, TLR3, TLR4, TLR5, and TLR9 ligands to induce production of IL-12, IL-6, and CXCL10 and second that NOD2 pre-stimulation of human DCs abolishes the subsequent ability of MDP to synergize with ligands of TLR3 and TLR9 in the induction of IL-12, IL-6, and TNF. That these "tolerogenic" effects of MDP pre-stimulation were in fact mediated by NOD2 was shown in parallel studies of murine BMDCs, that showed that NOD2 pre-stimulation of NOD2-deficient cells did not, whereas pre-stimulation of NOD2-intact cells did generate an inhibitory effect. Overall, these data provide strong evidence that NOD2 pre-stimulation of APCs negatively regulates inflammatory responses induced by a broad range of TLR ligands and therefore is another explanation of why defective NOD2 function contributes to the pathogenesis of Crohn's disease.

The present invention showed that IRF4 (19, 20), was induced by MDP signaling. Several subsequent studies presented herein showed that IRF4 is the mediator of NOD2 inhibition. First, silencing of IRF4 gene expression by either a mixture of or two individual IRF4-specific siRNAs abolished the inhibitory effect of NOD2 pre-stimulation on the human DC responses to TLR2 and TLR4 ligands. Second, neither NOD2 pre-stimulation of the human monocytic cell line, THP1 cells nor pre-stimulation of HT-29 epithelial cells did not inhibit subsequent cytokine responses to TLR ligands, consistent with the finding that both of these cells do not express IRF4. Third and most importantly, the protective effect of MDP administration on TNBS-colitis was abolished in mice administered intra-rectal IRF4-specific siRNA and the protective effect of MDP on DSS-colitis was abolished in IRF4-deficient mice. These in vitro and in vivo studies together provide strong evidence that IRF4 is indeed the major mediator of NOD2 inhibition.

Finally, it is important to note that this invention has implications with respect to how CARD15 mutations function as susceptibility factors in Crohn's disease (1). As shown in the study of NOD2-deficient mice reconstituted with plasmids expressing NOD2 reflecting a CARD15 frame-shift mutation, NOD2 resulting from a mutation does not confer MDP-mediated protection from DSS-colitis. These data, and the data obtained in NOD2-intact mice show that in patients with Crohn's disease-related CARD15 mutations, an important negative regulatory mechanism with respect to responses to the various TLR ligands associated with the normal mucosal microflora is impaired and the background innate immune response potentially induced by these ligands is correspondingly enhanced. While this in itself may not be sufficient to induce pathologic inflammation of the gastrointestinal tract, it could set the stage for such inflammation when a second abnormality is also present, such as a propensity to mount an adaptive immune response to one or another Ag associated with the intestinal microflora. This possibility is in fact supported by the recent finding that experimental colitis induced by an Ag present in a resident organism (OVA peptide expressed in recombinant *E. coli*) is facilitated in mice with deficient NOD2 expression (18). A further and more practical implication of the present findings relates to the fact that NOD2-ligand (MDP) administration to normal mice inhibits or abolishes induced experimental colitis. This finding shows that patients without NOD2 mutations can be treated with MDP to induce the down-regulation of innate responses to TLR ligands in the gastrointestinal tract.

Throughout this application, various publications are referenced. The disclosures of these publications in their entireties are hereby incorporated by reference into this application in order to more fully describe the state of the art to which this invention pertains.

REFERENCES

1. Strober, W., Murray, P. J., Kitani, A., and Watanabe, T. 2006. Signalling pathways and molecular interactions of NOD1 and NOD2. *Nat Rev Immunol* 6:9-20.
2. Watanabe, T., Kitani, A., and Strober, W. 2005. NOD2 regulation of Toll-like receptor responses and the pathogenesis of Crohn's disease. *Gut* 54:1515-1518.
3. Inohara, Chamaillard, McDonald, C., and Nunez, G. 2005. NOD-LRR proteins: role in host-microbial interactions and inflammatory disease. *Annu Rev Biochem* 74:355-383.
4. Hugot, J. P., Chamaillard, M., Zouali, H., Lesage, S., Cezard, J. P., Belaiche, J., Almer, S., Tysk, C., O'Morain, C. A., Gassull, M., et al. 2001. Association of NOD2 leucine-rich repeat variants with susceptibility to Crohn's disease. *Nature* 411:599-603.
5. Ogura, Y., Bonen, D. K., Inohara, N., Nicolae, D. L., Chen, F. F., Ramos, R., Britton, H., Moran, T., Karaliuskas, R., Duerr, R. H., et al. 2001. A frameshift mutation in NOD2 associated with susceptibility to Crohn's disease. *Nature* 411:603-606.
6. Inohara, N., Ogura, Y., Fontalba, A., Gutierrez, O., Pons, F., Crespo, J., Fukase, K., Inamura, S., Kusumoto, S., Hashimoto, M., et al. 2003. Host recognition of bacterial muramyl dipeptide mediated through NOD2. Implications for Crohn's disease. *J Biol Chem* 278:5509-5512.
7. Girardin, S. E., Boneca, I. G., Viala, J., Chamaillard, M., Labigne, A., Thomas, G., Philpott, D. J., and Sansonetti, P. J. 2003. Nod2 is a general sensor of peptidoglycan through muramyl dipeptide (MDP) detection. *J Biol Chem* 278: 8869-8872.
8. Marks, D. J., Harbord, M. W., MacAllister, R., Rahman, F. Z., Young, J., Al-Lazikani, B., Lees, W., Novelli, M., Bloom, S., and Segal, A. W. 2006. Defective acute inflammation in Crohn's disease: a clinical investigation. *Lancet* 367:668-678.
9. Dziarski, R., and Gupta, D. 2005. *Staphylococcus aureus* peptidoglycan is a toll-like receptor 2 activator: a reevaluation. *Infect Immun* 73:5212-38-5216.
10. Akira, S., Takeda, K., and Kaisho, T. 2001. Toll-like receptors: critical proteins linking innate and acquired immunity. *Nat Immunol* 2:675-680.
11. Watanabe, T., Kitani, A., Murray, P. J., and Strober, W. 2004. NOD2 is a negative regulator of Toll-like receptor 2-mediated T helper type 1 responses. *Nat Immunol* 5:800-808.
12. Bouma, G., and Strober, W. 2003. The immunological and genetic basis of inflammatory bowel disease. *Nat Rev Immunol* 3:521-533.
13. Strober, W., Fuss, I. J., and Blumberg, R. S. 2002. The immunology of mucosal models of inflammation. *Annu Rev Immunol* 20:495-549.
14. Mannon, P. J., Fuss, I. J., Mayer, L., Elson, C. O., Sandborn, W. J., Present, D., Dolin, B., Goodman, N., Groden, C., Hornung, R. L., et al. 2004. Anti-interleukin-12 antibody for active Crohn's disease. *N Engl J Med* 351:2069-2079.
15. Uehara, A., Yang, S., Fujimoto, Y., Fukase, K., Kusumoto, S., Shibata, K., Sugawara, S., and Takada, H. 2005. Muramyldipeptide and diaminopimelic acid-containing desmuramylpeptides in combination with chemically synthesized Toll-like receptor agonists synergistically induced production of interleukin-8 in a NOD2- and NOD1-dependent manner, respectively, in human monocytic cells in culture. *Cell Microbiol* 7:53-61.
16. Netea, M. G., Ferwerda, G., de Jong, D. J., Jansen, T., Jacobs, L., Kramer, M., Naber, T. H., Drenth, J. P., Girardin, S. E., Kullberg, B. J., et al. 2005. Nucleotide-binding oligomerization domain-2 modulates specific TLR pathways for the induction of cytokine release. *J Immunol* 174:6518-6523.
17. van Heel, D. A., Ghosh, S., Butler, M., Hunt, K. A., Lundberg, A. M., Ahmad, T., McGovern, D. P., Onnie, C., Negoro, K., Goldthorpe, S., et al. 2005. Muramyl dipeptide and toll-like receptor sensitivity in NOD2-associated Crohn's disease. *Lancet* 365:1794-1796.
18. Watanabe, T., Kitani, A., Murray, P. J., Wakatsuki, Y., Fuss, U., and Strober, W. 2006. Nucleotide binding oligomerization domain 2 deficiency leads to dysregulated TLR2 signaling and induction of antigen-specific colitis. *Immunity* 25:473-485.
19. Negishi, H., Ohba, Y., Yanai, H., Takaoka, A., Honma, K., Yui, K., Matsuyama, T., Taniguchi, T., and Honda, K. 2005. Negative regulation of Toll-like-receptor signaling by IRF-4. *Proc Natl Acad Sci USA* 102:15989-15994.
20. Honma, K., Udono, H., Kohno, T., Yamamoto, K., Ogawa, A., Takemori, T., Kumatori, A., Suzuki, S., Matsuyama, T., and Yui, K. 2005. Interferon regulatory factor 4 negatively regulates the production of proinflammatory cytokines by macrophages in response to LPS. *Proc Natl Acad Sci USA* 102:16001-16006.
21. Yang, Z., Fuss, I., Watanabe, T., Asano, N., Davey, M., Rosenbaum, J., Strober, W., and Kitani, A. 2007. NOD2 transgenic mice exhibit enhanced MDP-mediated Downregulation of TLR2 responses and resistance to colitis induction. *Gastroenterology* (in press).
22. Langenkamp, A., Messi, M., Lanzavecchia, A., and Sallusto, F. 2000. Kinetics of dendritic cell activation: impact on priming of TH1, TH2 and nonpolarized T cells. *Nat Immunol* 1:311-316.
23. Kobayashi, K., Hernandez, L. D., Galan, J. E., Janeway, C. A., Jr., Medzhitov, R., and Flavell, R. A. 2002. IRAK-M is a negative regulator of Toll-like receptor signaling. *Cell* 110:191-202.
24. Gingras, S., Parganas, E., de Pauw, A., Ihle, J. N., and Murray, P. J. 2004. Re-examination of the role of suppressor of cytokine signaling 1 (SOCS1) in the regulation of toll-like receptor signaling. *J Biol Chem* 279:54702-54707.
25. Lehtonen, A., Veckman, V., Nikula, T., Lahesmaa, R., Kinnunen, L., Matikainen, S., and Julkunen, I. 2005. Differential expression of IFN regulatory factor 4 gene in human monocyte-derived dendritic cells and macrophages. *J Immunol* 175:6570-6579.
26. Gutierrez, O., Pipaon, C., Inohara, N., Fontalba, A., Ogura, Y., Prosper, F., Nunez, G., and Fernandez-Luna, J. L. 2002. Induction of Nod2 in myelomonocytic and intestinal epithelial cells via nuclear factor-kappa B activation. *J Biol Chem* 277:41701-41705.
27. McDonald, C., Chen, F. F., Ollendorff, V., Ogura, Y., Marchetto, S., Lecine, P., Borg, J. P., and Nunez, G. 2005. A role for Erbin in the regulation of Nod2-dependent NF-kappaB signaling. *J Biol Chem* 280:40301-40309.
28. Yoshida, K., Yamamoto, K., Kohno, T., Hironaka, N., Yasui, K., Kojima, C., Mukae, H., Kadota, J., Suzuki, S., Honma, K., et al. 2005. Active repression of IFN regulatory factor-1-mediated transactivation by IFN regulatory factor-4. *Int Immunol* 17:1463-1471.
29. Tamura, T., Tailor, P., Yamaoka, K., Kong, H. J., Tsujimura, H., O'Shea, J. J., Singh, H., and Ozato, K. 2005. IFN regulatory factor-4 and -8 govern dendritic cell subset development and their functional diversity. *J Immunol* 174: 2573-2581.
30. Kobayashi, K. S., Chamaillard, M., Ogura, Y., Henegariu, O., Inohara, N., Nunez, G., and Flavell, R. A. 2005. Nod2-dependent regulation of innate and adaptive immunity in the intestinal tract. *Science* 307:731-734.
31. Maeda, S., Hsu, L. C., Liu, H., Bankston, L. A., Iimura, M., Kagnoff, M. F., Eckmann, L., and Karin, M. 2005. Nod2 mutation in Crohn's disease potentiates NF-kappaB activity and IL-1beta processing. *Science* 307:734-738.
32. Katakura, K., Lee, J., Rachmilewitz, D., Li, G., Eckmann, L., and Raz, E. 2005. Toll-like receptor 9-induced type I IFN protects mice from experimental colitis. *J Clin Invest* 115:695-702.
33. Rakoff-Nahoum, S., Hao, L., and Medzhitov, R. 2006. Role of toll-like receptors in spontaneous commensal-dependent colitis. *Immunity* 25:319-329.
34. Fichtner-Feigl, S., Fuss, I. J., Preiss, J. C., Strober, W., and Kitani, A. 2005. Treatment of murine Th1- and Th2-mediated inflammatory bowel disease with NF-kappa B decoy oligonucleotides. *J Clin Invest* 115:3057-3071.
35. Watanabe, T., Yamori, M., Kita, T., Chiba, T., and Wakatsuki, Y. 2005. CD4+CD25+ T cells regulate colonic localization of CD4 T cells reactive to a microbial antigen. *Inflamm Bowel Dis* 11:541-550.
36. Pauleau, A. L., and Murray, P. J. 2003. Role of nod2 in the response of macrophages to toll-like receptor agonists. *Mol Cell Biol* 23:7531-7539.
37. Watanabe, T., Katsukura, H., Shirai, Y., Yamori, M., Nishi, T., Chiba, T., Kita, T., and Wakatsuki, Y. 2003. A liver tolerates a portal antigen by generating CD11c+ cells, which select Fas ligand+ Th2 cells via apoptosis. *Hepatology* 38:403-412.
38. Kondrack, R. M., Harbertson, J., Tan, J. T., McBreen, M. E., Surh, C. D., and Bradley, L. M. 2003. Interleukin 7 regulates the survival and generation of memory CD4 cells. *J Exp Med* 198:1797-1806.
39. Watanabe, T., Yoshida, M., Shirai, Y., Yamori, M., Yagita, H., Itoh, T., Chiba, T., Kita, T., and Wakatsuki, Y. 2002. Administration of an antigen at a high dose generates regulatory CD4+ T cells expressing CD95 ligand and secreting IL-4 in the liver. *J Immunol* 168:2188-2199.
40. Obermeier, F., Kojouharoff, G., Hans, W., Scholmerich, J., Gross, V., and Falk, W. 1999. Interferon-gamma (IFN-gamma)- and tumour necrosis factor (TNF)-induced nitric oxide as toxic effector molecule in chronic dextran sulphate sodium (DSS)-induced colitis in mice. *Clin Exp Immunol* 116:238-245.
41. Neurath, M. F., Fuss, I., Kelsall, B. L., Stuber, E., and Strober, W. 1995. Antibodies to interleukin 12 abrogate established experimental colitis in mice. *J Exp Med* 182: 1281-1290.

What is claimed is:

1. A method of treating or of reducing by at least about 10% the onset, incidence, severity, or recurrence of inflammatory bowel disease or inflammation associated with inflammatory bowel disease in a subject comprising administering to the subject an effective amount of a composition comprising a muramyl dipeptide (MDP), wherein the inflammatory bowel disease is Crohn's disease or ulcerative colitis.

2. The method of claim 1, wherein the inflammatory bowel disease is Crohn's disease.

3. The method of claim 1, wherein the inflammatory bowel disease is ulcerative colitis.

4. The method of claim 1, wherein the subject is a human.

5. A method of reducing the symptoms of inflammatory bowel disease by modulating IRF4 production, comprising administering to the subject an amount of a composition comprising a muramyl dipeptide (MDP) effective in modulating IRF4 production, thereby reducing the symptoms of inflammatory bowel disease wherein the inflammatory bowel disease is Crohn's disease or ulcerative colitis.

6. The method of claim 5, wherein the inflammatory bowel disease is Crohn's disease.

7. The method of claim 5, wherein the inflammatory bowel disease is ulcerative colitis.

8. The method of claim 5, wherein the subject is a human.

* * * * *

SEQUENCE LISTING

<160> NUMBER OF SEQ ID NOS: 5

<210> SEQ ID NO 1
<211> LENGTH: 47

```
-continued

<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 1
cagaagccct cctgcaggcc ccttaaggga acagtgccat tctggag                    47

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 2
cuccuuuccu aucuuuacau u                                                21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 3
gguagguauu aguguuugau u                                                21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 4
uaaggcuaug aagagauacu u                                                21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 5
ggacacaccu augauguuau u                                                21
```